US012144808B2

(12) United States Patent
Li et al.

(10) Patent No.: US 12,144,808 B2
(45) Date of Patent: Nov. 19, 2024

(54) COMPOSITIONS AND METHODS

(71) Applicant: INTRA-CELLULAR THERAPIES, INC., New York, NY (US)

(72) Inventors: Peng Li, New Milford, NJ (US); Robert Davis, San Diego, CA (US)

(73) Assignee: INTRA-CELLULAR THERAPIES, INC., Bedminster, NJ (US)

( * ) Notice: Subject to any disclaimer, the term of this patent is extended or adjusted under 35 U.S.C. 154(b) by 730 days.

(21) Appl. No.: 17/271,965

(22) PCT Filed: Aug. 29, 2019

(86) PCT No.: PCT/US2019/048785
§ 371 (c)(1),
(2) Date: Feb. 26, 2021

(87) PCT Pub. No.: WO2020/047241
PCT Pub. Date: Mar. 5, 2020

(65) Prior Publication Data
US 2021/0315891 A1 Oct. 14, 2021

Related U.S. Application Data

(60) Provisional application No. 62/724,472, filed on Aug. 29, 2018.

(51) Int. Cl.
*A61K 31/4985* (2006.01)
*A61K 9/70* (2006.01)

(52) U.S. Cl.
CPC ........ *A61K 31/4985* (2013.01); *A61K 9/7084* (2013.01)

(58) Field of Classification Search
None
See application file for complete search history.

(56) References Cited

U.S. PATENT DOCUMENTS

| | | | |
|---|---|---|---|
| 2,490,813 A | 12/1949 | Hughes et al. |
| 3,299,078 A | 1/1967 | Pachter |
| 3,813,392 A | 5/1974 | Sellstedt et al. |
| 3,914,421 A | 10/1975 | Rajagopalan |
| 4,001,263 A | 1/1977 | Plattner et al. |
| 4,115,577 A | 9/1978 | Rajagopalan |
| 4,136,145 A | 1/1979 | Fuchs et al. |
| 4,183,936 A | 1/1980 | Rajagopalan |
| 4,219,550 A | 8/1980 | Rajagopalan |
| 4,238,607 A | 12/1980 | Rajagopalan |
| 4,389,330 A | 6/1983 | Tice et al. |
| 4,522,944 A | 6/1985 | Doria et al. |
| 4,530,840 A | 7/1985 | Tice et al. |
| 4,849,246 A | 7/1989 | Schmidt |
| 4,971,971 A | 11/1990 | Tokunaga et al. |
| 4,985,432 A | 1/1991 | Tokunaga et al. |
| 5,114,976 A | 5/1992 | Norden |
| 5,151,419 A | 9/1992 | Perenyi et al. |
| 5,538,739 A | 7/1996 | Bodmer et al. |
| 5,576,460 A | 11/1996 | Buchwald et al. |
| 5,629,003 A | 5/1997 | Horstmann et al. |
| 5,648,539 A | 7/1997 | Goodbrand |
| 5,648,542 A | 7/1997 | Goodbrand et al. |
| 5,654,482 A | 8/1997 | Goodbrand |
| 5,705,697 A | 1/1998 | Goodbrand et al. |
| 5,723,669 A | 3/1998 | Goodbrand et al. |
| 5,723,671 A | 3/1998 | Goodbrand et al. |
| 5,763,476 A | 6/1998 | Delbressine et al. |
| 5,847,166 A | 12/1998 | Buchwald et al. |
| 5,902,901 A | 5/1999 | Goodbrand et al. |
| 5,948,430 A | 9/1999 | Zerbe et al. |
| 6,043,370 A | 3/2000 | Kubo et al. |
| 6,166,226 A | 12/2000 | Buchwald et al. |
| 6,221,335 B1 | 4/2001 | Foster |
| 6,235,936 B1 | 5/2001 | Buchwald et al. |
| 6,307,087 B1 | 10/2001 | Buchwald et al. |
| 6,323,366 B1 | 11/2001 | Wolfe et al. |
| 6,395,916 B1 | 5/2002 | Buchwald et al. |
| 6,407,092 B1 | 6/2002 | Hester et al. |
| 6,440,710 B1 | 8/2002 | Keinan et al. |
| 6,465,693 B2 | 10/2002 | Buchwald et al. |
| 6,541,639 B2 | 4/2003 | Zhou et al. |
| 6,544,559 B2 | 4/2003 | Mesens et al. |

(Continued)

FOREIGN PATENT DOCUMENTS

| | | |
|---|---|---|
| EP | 0 058 481 | 8/1982 |
| EP | 0 856 508 | 8/1998 |

(Continued)

OTHER PUBLICATIONS

Alkilani, A.Z., et al., "Transdermal Drug Delivery: Innovative Pharmaceutical Developments Based on Disruption of the Barrier Properties of the Stratum Corneum," *Pharmaceutics*, vol. 7, pp. 438-470, (2015).

Aiken, "An Overview of Atypical Antipsychotics for Bipolar Depression," published on Jan. 3, 2020 at https://www.psychiatrictimes.com/view/overview-atypical-antipsychotics-bipolar-depression, 11 pages.

Alvir, et al., "Clozapine-Induced Agranulocytosis," *The New England Journal of Medicine*, vol. 329, No. 3, pp. 162-167, (1993).

(Continued)

*Primary Examiner* — Celeste A Roney
(74) *Attorney, Agent, or Firm* — Hoxie & Associates LLC

(57) ABSTRACT

The disclosure provides new transdermal pharmaceutical compositions comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one or 1-(4-fluoro-phenyl)-4-((6bR,10aS)-2,2-d$_2$-3-methyl-2,3,6b,9,10,10a-hexahydro-1H,7H-pyrido[3',4':4,5]pyrrolo[1,2,3-de]quinoxalin-8-yl)-butan-1-one or comprising -(4-fluoro-phenyl)-4-((6bR,10aS)-1,1,2,2-d$_4$-3-methyl-2,3,6b,9,10,10a-hexahydro-1H,7H-pyrido[3',4':4,5]pyrrolo[1,2,3-de]quinoxalin-8-yl)-butan-1-one, in free base, co-crystal or salt form, together with methods of making and using them.

31 Claims, No Drawings

(56) References Cited

U.S. PATENT DOCUMENTS

| | | |
|---|---|---|
| 6,548,493 B1 | 4/2003 | Robichaud et al. |
| 6,552,017 B1 | 4/2003 | Robichaud et al. |
| 6,552,024 B1 | 4/2003 | Chen et al. |
| 6,603,008 B1 | 8/2003 | Ando et al. |
| 6,699,852 B2 | 3/2004 | Robichaud et al. |
| 6,713,471 B1 | 3/2004 | Robichaud et al. |
| 6,723,732 B1 | 4/2004 | Sugita et al. |
| 6,759,554 B2 | 7/2004 | Buchwald et al. |
| 6,762,329 B2 | 7/2004 | Marcoux et al. |
| 6,828,314 B2 | 12/2004 | Frank et al. |
| 6,849,619 B2 | 2/2005 | Robichaud et al. |
| 6,849,640 B2 | 2/2005 | Ennis et al. |
| 6,867,298 B2 | 3/2005 | Buchwald et al. |
| 6,888,032 B2 | 5/2005 | Buchwald et al. |
| 6,946,560 B2 | 9/2005 | Buchwald et al. |
| 7,026,498 B2 | 4/2006 | Buchwald et al. |
| 7,071,186 B2 | 7/2006 | Robichaud et al. |
| 7,109,339 B2 | 9/2006 | Lee et al. |
| 7,115,784 B2 | 10/2006 | Buchwald et al. |
| 7,183,282 B2 | 2/2007 | Robichaud et al. |
| 7,223,879 B2 | 5/2007 | Buchwald et al. |
| RE39,679 E | 6/2007 | Robichaud et al. |
| RE39,680 E | 6/2007 | Robichaud et al. |
| 7,238,690 B2 | 7/2007 | Robichaud et al. |
| 7,247,731 B2 | 7/2007 | Buchwald et al. |
| 7,323,608 B2 | 1/2008 | Buchwald et al. |
| 7,375,226 B2 | 5/2008 | Jolidon et al. |
| 7,404,965 B2 * | 7/2008 | Carrara .............. A61K 31/551 424/464 |
| 7,462,641 B2 | 12/2008 | Igo et al. |
| 7,517,990 B2 | 4/2009 | Ito et al. |
| 7,592,454 B2 | 9/2009 | Lee et al. |
| 7,614,727 B2 | 11/2009 | Hori |
| 7,645,752 B2 | 1/2010 | McDevitt et al. |
| 7,998,971 B2 | 8/2011 | Barlow et al. |
| 8,309,722 B2 | 11/2012 | Tomesch et al. |
| 8,354,121 B2 | 1/2013 | Maeda et al. |
| 8,414,922 B2 | 4/2013 | Bryson et al. |
| 8,461,148 B2 | 6/2013 | Hollander |
| 8,603,514 B2 | 12/2013 | Yang et al. |
| 8,652,378 B1 | 2/2014 | Yang et al. |
| 8,697,700 B2 | 4/2014 | Surman et al. |
| 8,779,139 B2 | 7/2014 | Tomesch et al. |
| 8,791,138 B2 | 7/2014 | Seeman et al. |
| 8,835,459 B2 | 9/2014 | Kottayil et al. |
| 8,900,497 B2 | 12/2014 | Yang et al. |
| 8,900,498 B2 | 12/2014 | Yang et al. |
| 8,906,277 B2 | 12/2014 | Yang et al. |
| 9,108,340 B2 | 8/2015 | Yang et al. |
| 9,168,258 B2 | 10/2015 | Mates et al. |
| 9,199,995 B2 | 12/2015 | Tomesch et al. |
| 9,216,175 B2 | 12/2015 | Amancha et al. |
| 9,315,504 B2 | 4/2016 | Tomesch et al. |
| 9,371,324 B2 | 6/2016 | Mates et al. |
| 9,393,192 B2 | 7/2016 | Yam et al. |
| 9,427,412 B2 | 8/2016 | Bryson et al. |
| 9,567,327 B2 | 2/2017 | Xiong et al. |
| 9,586,960 B2 | 3/2017 | Tomesch et al. |
| 9,616,061 B2 | 4/2017 | Mates et al. |
| 9,708,322 B2 | 7/2017 | Li et al. |
| 9,745,300 B2 | 8/2017 | Mates et al. |
| 9,751,883 B2 | 9/2017 | Tomesch et al. |
| 9,956,227 B2 | 5/2018 | Vanover et al. |
| 10,072,010 B2 | 9/2018 | Li et al. |
| 10,077,267 B2 | 9/2018 | Mates et al. |
| 10,117,867 B2 | 11/2018 | Mates et al. |
| 10,654,854 B2 | 5/2020 | Li et al. |
| 10,688,097 B2 | 6/2020 | Yao et al. |
| 10,716,786 B2 | 7/2020 | Li et al. |
| 2001/0008942 A1 | 7/2001 | Buchwald et al. |
| 2004/0034015 A1 | 2/2004 | Robichaud et al. |
| 2004/0092534 A1 | 5/2004 | Yam et al. |
| 2004/0127482 A1 | 7/2004 | Robichaud et al. |
| 2004/0142970 A1 | 7/2004 | Chung et al. |
| 2004/0180875 A1 | 9/2004 | Lee et al. |
| 2004/0186136 A1 | 9/2004 | Alken et al. |
| 2004/0209864 A1 | 10/2004 | Robichaud et al. |
| 2005/0166771 A1 | 8/2005 | Gygi et al. |
| 2005/0222209 A1 | 10/2005 | Zeldis et al. |
| 2005/0222238 A1 | 10/2005 | Alken |
| 2006/0178362 A1 | 8/2006 | Robichaud et al. |
| 2006/0205787 A1 | 9/2006 | Muller et al. |
| 2007/0082929 A1 | 4/2007 | Gant et al. |
| 2007/0197695 A1 | 8/2007 | Potyen et al. |
| 2007/0254877 A1 | 11/2007 | Nishikimi et al. |
| 2008/0069885 A1 | 3/2008 | Mesens et al. |
| 2008/0132552 A1 | 6/2008 | Kleinman et al. |
| 2008/0280941 A1 | 11/2008 | Lourtie |
| 2009/0076159 A1 | 3/2009 | Czarnik |
| 2009/0209608 A1 | 8/2009 | Czarnik |
| 2010/0113781 A1 | 5/2010 | Tomesch et al. |
| 2010/0159033 A1 | 6/2010 | Gant et al. |
| 2011/0071080 A1 | 3/2011 | Mates et al. |
| 2011/0112105 A1 | 5/2011 | Tomesch et al. |
| 2012/0196814 A1 | 8/2012 | Gong et al. |
| 2013/0202692 A1 | 8/2013 | Mates et al. |
| 2014/0050783 A1 * | 2/2014 | Mates .................. A61K 9/0053 514/250 |
| 2014/0210117 A1 | 7/2014 | Friesen et al. |
| 2015/0004237 A1 | 1/2015 | Edgar et al. |
| 2015/0031804 A1 | 1/2015 | Shiramizu et al. |
| 2015/0072964 A1 | 3/2015 | Mates et al. |
| 2015/0079172 A1 | 3/2015 | Mates et al. |
| 2015/0080404 A1 | 3/2015 | Mates et al. |
| 2016/0235720 A1 | 8/2016 | Foster et al. |
| 2016/0354315 A1 | 12/2016 | Li |
| 2017/0114037 A1 | 4/2017 | Davis et al. |
| 2017/0183350 A1 | 6/2017 | Mates et al. |
| 2017/0189398 A1 | 7/2017 | Mates et al. |
| 2017/0283417 A1 | 10/2017 | Li et al. |
| 2017/0319580 A1 | 11/2017 | Yao et al. |
| 2018/0044337 A1 | 2/2018 | Tomesch et al. |
| 2018/0200256 A1 | 7/2018 | Vanover et al. |
| 2019/0071445 A1 | 3/2019 | Li et al. |
| 2019/0183888 A1 | 6/2019 | Mates et al. |
| 2019/0231780 A1 | 8/2019 | Yao et al. |
| 2019/0388418 A1 | 12/2019 | Li |
| 2020/0179298 A1 * | 6/2020 | Mohr .................. A61K 9/7069 |
| 2020/0392135 A1 | 12/2020 | Wennogle et al. |

FOREIGN PATENT DOCUMENTS

| | | |
|---|---|---|
| EP | 0 976 732 | 2/2000 |
| EP | 1 245 553 | 10/2002 |
| EP | 1 254 884 | 11/2002 |
| EP | 1 539 115 | 6/2005 |
| EP | 1 564 671 | 8/2005 |
| GB | 1476087 | 6/1977 |
| GB | 2145422 | 3/1985 |
| RU | 2465267 | 10/2012 |
| WO | WO 1994/024125 | 10/1994 |
| WO | WO 1995/013814 | 5/1995 |
| WO | WO 1995/026325 | 10/1995 |
| WO | WO 1998/015515 | 4/1998 |
| WO | WO 1998/043956 | 10/1998 |
| WO | WO 1999/043643 | 9/1999 |
| WO | WO 2000/002887 | 1/2000 |
| WO | WO 2000/035419 | 6/2000 |
| WO | WO 2000/048610 | 8/2000 |
| WO | WO 2000/064899 | 11/2000 |
| WO | WO 2000/077001 | 12/2000 |
| WO | WO 2000/077002 | 12/2000 |
| WO | WO 2000/077010 | 12/2000 |
| WO | WO 2002/059129 | 8/2002 |
| WO | WO 2002/085838 | 10/2002 |
| WO | WO 2003/014118 | 2/2003 |
| WO | WO 2004/010981 | 2/2004 |
| WO | WO 2004/013094 | 2/2004 |
| WO | WO 2004/039788 | 5/2004 |
| WO | WO 2004/045668 | 6/2004 |
| WO | WO 2004/056324 | 7/2004 |
| WO | WO 2005/030214 | 4/2005 |
| WO | WO 2006/034187 | 3/2006 |
| WO | WO 2006/081251 | 8/2006 |

(56) References Cited

FOREIGN PATENT DOCUMENTS

| WO | WO 2006/081332 | 8/2006 |
|---|---|---|
| WO | WO 2007/084841 | 7/2007 |
| WO | WO 2009/017836 | 2/2009 |
| WO | WO 2009/100324 | 8/2009 |
| WO | WO 2012/105623 A1 | 8/2012 |
| WO | WO 2014/110322 | 7/2014 |
| WO | WO 2017/117514 | 7/2017 |
| WO | WO 2018/031535 | 2/2018 |
| WO | WO 2018/106916 | 6/2018 |
| WO | WO 2018/189646 | 10/2018 |
| WO | WO 2019/102240 | 5/2019 |

OTHER PUBLICATIONS

Angst et al. "Prevalence and Characteristics of Undiagnosed Bipolar Disorders in Patients With a Major Depressive Episode", Arch Gen Psychiatry, vol. 68, No. 8, pp. 701-709, (2011).
Avendano, et al., "The problem of the existence of C(Ar)-H . . . N Intramolecular Hydrogen Bonds in a Family of 9-Azaphenyl-9H-carbazoles," J. Chem. Soc. Perkin Trans., vol. 2, pp. 1547-1555, (1993).
Baille, T.A., "The Use of Stable Isotopes in Pharmacological Research," Pharmacol. Reviews, vol. 33, No. 2, pp. 81-132, (1981).
Balbach, et al., "Pharmaceutical evaluation of early development candidates 'the 100 mg-approach'," International Journal of Pharmaceutics, vol. 275, pp. 1-12, (2004).
Bastin, et al.,"Salt Selection and Optimisation Procedures for Pharmaceutical New Chemical Entities," Organic Process and Research Development, vol. 4, No. 5, pp. 427-435 (2000).
Beletskaya, et al., "Pd- and Cu-catalyzed selective arylation of benzotriazole," Tetrahedron Letters, vol. 39, pp. 5617-5620, (1998).
Bechtold et al., "Circadian Dysfunction in Disease," Trends in Pharmacological Sciences, vol. 31, No. 5, pp. 191-198, (2010); DOI: 10.1016/j.tips.2010.01.002; Abstract Only.
Bennett, et al., "Cecil Textbook of Medicine," 20th Edition, vol. 1, pp. 1004-1010, (1996).
Berger, et al., "Synthesis of Some Conformationally Restricted Analogs of Fentanyl," Journal of Medicinal Chemistry, vol. 20, No. 4, pp. 600-602, (1977).
Boger, et al., "Inverse Electron Demand Diels-Alder Reactions of Heterocyclic Aza Dienes. Studies on the Total Synthesis of Lavendamyin: Investigative Studies on the Preparation of the CDE β-Carboline Ring System and AB Quinoline-5,8-quinone Ring System," J. Org. Chem., vol. 50, pp. 5782-5789, (1985).
Borghans et al., "Animal Models for Posttraumatic Stress Disorder: An Overview of What is Used in Research," World J. Psychiatr., vol. 5, No. 4, pp. 387-396, (2015); DOI: 10.5498/wjp.v5.i4.387.
Bowman, et al., "Intramolecular Aromatic Substitution ($S_{RN}1$) Reactions—Use of Entrainment for the Preparation of Benzothiazoles," Tetrahedron Letters, vol. 23, pp. 5093-5096, (1982).
Bowman, et al., "Copper (1) Catalysed Aromatic Nucleophilic Substitution: A Mechanistic and Synthetic Comparison with the $S_{RN}1$ Reaction," Tetrahedron Letters, vol. 25, No. 50, pp. 5821-5824, (1984).
Bowman, et al.,"Synthesis of 1H-quinazoline-4-ones Using Intramolecular Aromatic Nucelophilic Substitution," ARKIVOC, vol. x, pp. 434-442 (2003).
Bremner, et al., "Neuroimaging of Posttraumatic Stress Disorder", Psychiatric Annals Journal, vol. 28, No. 8, p. 445-450, (1998).
Browne, T.R., "Stable Isotope Techniques in Early Drug Development: An Economic Evaluation," J. Clin. Pharmacol., vol. 38, pp. 213-220, (1998).
Bryan-Lluka, et al., "Potencies of Haloperidol Metabolites as Inhibitors of the Human Noradrenaline, Dopamine and Serotonin Transporters in Transfected COS-7 Cells," Naunyn-Shemiedeberg's Arch Pharmacol, vol. 360, pp. 109-115, (1999).
Byrn, et al., "Pharmaceutical Solids: A Strategic Approach to Regulatory Considerations," Pharmaceutical Research, vol. 12, No. 7, pp. 945-954, (1995).
Caira, M.R., "Crystalline Polymorphism of Organic Compounds," Topics in Current Chemistry, vol. 198, p. 163-203, (1998).
Cherrah, et al., "Study of Deuterium Isotope Effects on Protein Binding by Gas Chromatography/Mass Spectrometry. Caffeine and Deuterated Isotopomers," Biomedical and Environmental Mass Spectrometry, vol. 14, pp. 653-657, (1987).
Crawford, et al., "Copper-Catalyzed Amidations of Bromo Substituted Furans and Thiophenes," Tetrahedron Letters, vol. 43, pp. 7365-7368, (2002).
Darmani, et al., "Do Functional Relationships Exist Between 5-$HT_{1A}$ and 5-$HT_2$ Receptors?" Pharmacology and Biochemistry & Behavior, vol. 36, pp. 901-906, (1990).
Davis, et al., "ITI-007 demonstrates brain occupancy at serotonin 5-$HT_{2A}$ and dopamine $D_2$ receptors and serotonin transporters using positron emission tomography in healthy volunteers," Psychopharmacology, vol. 232, pp. 2863-2872, (2015); DOI: 10.1007/s00213-015-3922-1.
Davis, et al., "ITI-007 in the Treatment of Schizophrenia: From Novel Pharmacology to Clinical Outcomes," Expert Review of Neurotherapeutics, vol. 16, No. 6, pp. 601-614, (2016).
Davis et al., "ITI-007: A Novel Treatment for Behavioral Disturbances Associated with Dementia and Related Disorders," Clinical Trials in Alzheimer's Disease (CTAD) Congress 2014 (2014) (poster presentation).
Davis et al., "Rationale for the Development of Low Doses of ITI-007 for the Treatment of Behavioral Disturbances Associated with Dementia," The Journal of Prevention of Alzheimer's Disease, 2(4):302 (2015) (Clinical Trials in Alzheimer's Disease (CTAD) Congress, Symposium Summary OC51).
Davis, et al., "Lumateperone (ITI-007), A Novel Drug in Development for the Treatment of Agitation in Patients with Dementia, including Alzheimer's Disease: Rationale and Clinical Design," The Journal of Prevention of Alzheimer's Disease, 4(4):372 (2017) (Clinical Trials in Alzheimer's Disease (CTAD) Congress, Symposium Summary p. 93.
Dyck, et al., "Effects of Deuterium Substitution on the Catabolismof β-Phenylethylamine: An In Vivo Study," Journal of Neurochemistry, vol. 46, Issue 2, pp. 399-404, (1986).
Ellenbroek et al., "Animal Models for the Negative Symptoms of Schizophrenia," Behavioural Pharmacology, vol. 11, pp. 223-233, (2000).
Evindar, et al., "Copper- and Palladium-Catalyzed Intramolecular Aryl Guanidinylation: An Efficient Method for the Synthesis of 2-Aminobenzimidazoles", Organic Letters, vol. 5, No. 2, pp. 133-136, (2003).
Ezquerra, et al., "Efficient Reagents for the Synthesis of 5-, 7-, and 5, 7-Substitued Indoles Starting from Aromatic Amines: Scope and Limitations", J. Org. Chem., vol. 61, pp. 5804-5812, (1996).
Fawcett, J., "Posttraumatic Stress Disorder, Stress, and Happiness", Psychiatric Annals Journal, vol. 28, No. 8, pp. 427-428, (1998).
Fee, et al., "Copper (II)-Promoted Solvolyses of Nickel (II) Complexes III. Tetradentate Schiff Base Ligands Containing Various Diamine Segments," Aust. J. Chem., vol. 26, pp. 1475-1485, (1973).
Ferreira, et al., "Novel Synthetic Routes to Thienocarbazoles Via Palladium or Copper Catalyzed Amination or Amidation of Arylhalides and Intramolecular Cyclization", Tetrahedron, vol. 58, pp. 7943-7949, (2002).
Finet, et al., "Recent Advances in Ullmann Reaction: Copper (II) Diacetate Catalysed N-, )- and S-arylation Involving Polycoordinate Heteroatomic Derivatives," Current Organic Chemistry, vol. 6, pp. 597-626, (2002).
Fletcher et al., "Perceiving is Believing: A Bayesian Approach to Explaining the Positive Symptoms of Schizophrenia," Nature Reviews/Neuroscience, vol. 10, pp. 48-58, (2009).
Foster, et al., "Acetylcholinesterase Inhibitors Reduce Spreading Activation in Dementia," Neuropsychologia, vol. 50, pp. 2093-2099, (2012).
Friedman, M.J .. , "Current and Future Drug Treatment for Post-traumatic Stress Disorder Patients", Psychiatric Annals Journal, vol. 28, No. 8, pp. 464-468, (1998).
Goodbrand, et al., "Ligand-Accelerated Catalysis of the Ullmann Condensation: Application to Hole Conducting Triarylamines," J. Org. Chem., vol. 64, pp. 670-674, (1999).

(56) References Cited

OTHER PUBLICATIONS

Gouyette, A., "Synthesis of Deuterium-labelled Elliptinium and its Use in Metabolic Studies," *Biomedical and Environmental Mass Spectrometry*, vol. 15, pp. 243-247, (1988).
Gramigna, "Lumateperone Safe, Effective for Depressive Symptoms Among Patients with Bipolar Disorders," American Society of Clinical Psychopharmacology Annual Meeting, Jun. 2, 2020, 3 pages.
Grant, D., "Theory and Origin and Polymorphism", *Polymorphism in Pharmaceutical Solids*, Chapter 1, pp. 1-10, (1999).
Guillory, J.K., "Generation of Polymorphs, Hydrates, Solvates, and Amorphous Solids", *Polymorphism in Pharmaceutical Solids*, Chapter 5, pp. 183-226, (1999).
Hackam, et al., "Translation of Research Evidence from Animals to Humans," *JAMA*, vol. 296, No. 14, pp. 1731-1732, (2006).
Hamann, et al., "Systematic Variation of Bidentate Ligands Used in Aryl Halide Amination. Unexpected Effects of Steric, Electronic, and Geometric Perturbations", *J. Am. Chem. Soc.*, vol. 120, pp. 3694-3703, (1998).
Harbert, et al., "Neuroleptic Activity in 5-Aryltetrahydro-γ-carbolines", *J. Med. Chem.*, vol. 23, pp. 635-643, (1980).
Hartwig, J., "Palladium-Catalyzed Amination of Aryl Halides: Mechanism and Rational Catalyst Design," *Synlett*, pp. 329-340, (1996).
Harvey, et al., "Serotonin and Stress: Protective or Malevolent Actions in the Biobehavioral Response to Repeated Trauma?," *Annals of the New York Academy of Sciences*, vol. 1032, pp. 267-272, (2004); DOI: 10.1196/annals.1314.035.
Haskins, N.J., "The Application of Stable Isotopes in Biomedical Research," *Biological Mass Spectrometry*, vol. 9, No. 7, pp. 269-277, (1982).
Hassan, et al., "Aryl-aryl Bond Formation One Century After the Discovery of the Ullmann Reaction," *Chem. Rev.*, vol. 102, pp. 1359-1469, (2002).
Haynes, et al., "Occurrence of Pharmaceutically Acceptable Anions and Cations in the Cambridge Structural Database", *Journal of Pharmaceutical Sciences*, vol. 94, No. 10, pp. 2111-2120, (2005).
Hlavinka, "Schizophrenia Tx Eases Depression in Bipolar Disorder: Lumateperone Offers Greater Rate of Response, Remission versus Placebo," Medpage Today, 7 pages, (2020); https://www.medpagetoday.com/meetingcoverage/psychcongress/88584.
Honma, S., et al., "The Metabolism of Roxatidine Acetate Hydrochloride: Liberation of Deuterium from the Piperidine Ring during Hydroxylation," *Drug Metabolism and Disposition*, vol. 15, No. 4, pp. 551, (1987).
Howland, R.H., "Deuterated Drugs," Journal of Psychosocial Nursing and Mental Health Services, 53(9): 13-16 (2015).
International Preliminary Report on Patentability for International Application No. PCT/US2013/036514 issued Oct. 14, 2014.
International Search Report issued in International Application No. PCT/US2008/003340, mailed Aug. 8, 2008, 3 pages.
International Search Report issued in International Application No. PCT/US2009/001608, mailed Apr. 27, 2009, 3 pages.
International Search Report issued in International Application No. PCT/US2009/003261, mailed Jul. 16, 2009.
International Search Report issued in International Application No. PCT/US2011/00719, mailed Jul. 5, 2011, 3 pages.
International Search Report issued in International Application No. PCT/US2013/036515, mailed Aug. 13, 2013, 3 pages.
International Search Report issued in International Application No. PCT/US2013/036514, mailed Aug. 16, 2013, 3 pages.
International Search Report issued in International Application No. PCT/US2013/036512, mailed Aug. 19, 2013, 4 pages.
International Search Report issued in International Application No. PCT/US2015/024340, mailed Jun. 25, 2015, 2 pages.
International Search Report issued in International Application No. PCT/US2015/024345, mailed Jun. 25, 2015, 3 pages.
International Search Report issued in International Application No. PCT/US2017/054962, date mailed Nov. 27, 2017, 3 pages.
Ito, et al., "Studies of Organic Catalytic Reactions. VI. The Function of Pyridine and Copper in the Rosenmund-von Braun Reaction," *Bulletin of the Chemical Society of Japan*, vol. 41, pp. 419-423, (1968).
Izrayelit, L., "Schizoaffective Disorder and PTSD Successfully Treated With Olanzapine and Supportive Psychotherapy", *Psychiatric Annals Journal*, vol. 28, No. 8, pp. 424-426, (1998).
Jain et al., "Polymorphism in Pharmacy," *Indian Drugs*, vol. 23, No. 6, pp. 315-316, (1986).
Ji, et al., "Selective Amination of Polyhalopyridines Catalyzed by a Palladium-xantphos Complex," *Organic Letters*, vol. 5, No. 24, pp. 4611-4614, (2003).
Johnson et al., "Serotonin receptor activity is necessary for olfactory learning and memory in Drosophila melanogaster," *Neuroscience*, vol. 192, pp. 372-381 (2011).
Jordan, V.C., "Tamoxifen: A Most Unlikely Pioneering Medicine," *Nature Reviews: Drug Discovery*, vol. 2, pp. 205-213, (2003).
Juorio, A.V., et al., "Effects of Acute and Chronic Phenelzine on Regional Monoamine Metabolism in Rats and its Potentiation by Deuterium Substitution," *Naunyn-Schmiedeberg's Archives of Pharmacology*, vol. 333, No. 3, pp. 240-245, (1986); Abstract only.
Kahn et al., "Residual Symptoms of Schizophrenia. What are Realistic Treatment Goals? Lingering Symptoms Require you to Evaluate Pharmacotherapy and Offer Psychosocial Interventions," *Current Psychiatry*, vol. 16, No. 3, pp. 35-40, (2017).
Kametani, et al., "A Novel Synthesis of Indole Derivatives," *Heterocycles*, vol. 14 No. 3, pp. 277-280, (1980).
Kang, et al., "Copper-catalyzed N-arylation of Aryl Iodides with Benzamides or Nitrogen Heterocycles in the Presence of Ethylendiamine," *Synlett*, No. 3, pp. 427-430, (2002).
Kay, et al., "The Positive and Negative Syndrome Scale (PANSS) for Schizophrenia," *Schizophrenia Bulletin*, vol. 13, No. 2, pp. 261-276, (1987).
Kessler, et al., "Lifetime Prevalence and Age-of-Onset Distributions of DSM-IV Disorders in the National Comorbidity Survey Replication," *Arch Gen Psychiatry*, vol. 62, pp. 593-602, (2005).
Khorana, et al., "Gamma-Carbolines: Binding at 5-HT5A Serotonin Receptors," *Bioorganic & Medicinal Chemistry*, vol. 11, pp. 717-722, p. 718 Table 1, (2003).
Kiyomori, et al., "An Efficient Copper-catalyzed Coupling of Aryl Halides with Imidazoles," *Tetrahedron Letters*, vol. 40, pp. 2657-2660, (1999).
Klapars, et al., "A General and Efficient Copper Catalyst for the Amidation of Aryl Halides and the N-arylation of Nitrogen Heterocycles," *J. Am. Chem. Soc.*, vol. 123, pp. 7727-7729, (2001).
Klapars, et al., "A General and Efficient Copper Catalyst for the Amidation of Aryl Halides," *J. Am. Chem. Soc.*, vol. 124, pp. 7421-7428, (2002).
Kondratov, et al., "Nucelophilic Substitution in the Aromatic Series. Lv. Reaction of o-nitrochlorobenzene with Ammonia in the Presence of Copper Compounds," *Zhurnal Organidreskoi Khimii*, vol. 51, No. 11, pp. 2387-2390, (1979).
Koppel, et al., "Optimal Treatment of Alzheimer's Disease Psychosis: Challenges and Solutions," *Neuropsychiatric Disease and Treatment*, vol. 10, pp. 2253-2262, (2014).
Krystal et al., "Adjunctive Risperidone Treatment for Antidepressant-Resistant Symptoms of Chronic Military Service-Related PTSD: A Randomized Trial," *JAMA*, vol. 306, No. 5, pp. 493-502, (2011).
Kwong, et al., "Mild and Efficient Copper-catalyzed Amination of Aryl Bromides with Primary Alkylamines," *Organic Letters*, vol. 5, No. 6, pp. 793-796, (2003).
Lammers et al., "Risperidone Long-acting Injection in Schizophrenia Spectrum Illnesses Compared to First Generation Depot Antipsychotics in an Outpatient Setting in Canada," *BMC Psychiatry*, vol. 13, No. 155, 9 pages, (2013); http://www.biomedcentral.com/1471-244X/13/155.
Lebert, et al., "Trazodone in Fronto-Temporal Dementia," *Research and Practice in Alzheimer's Disease*, vol. 11, pp. 356-360, (2006).
Lee, et al. "Novel, Highly Potent, Selective 5-$HT_{2A}$/$D_2$ Receptor Antagonists as Potential Atypical Antipsychotics," *Bioorg. Med. Chem. Lett.*, vol. 13, pp. 767-770, (2003).
Li, et al., "Discovery of a Tetracyclic Quinoxaline Derivative as a Potent and Orally Active Multifunctional Drug Candidate for the

(56) References Cited

OTHER PUBLICATIONS

Treatment of Neuropsychiatric and Neurological Disorders," *Journal of Medicinal Chemistry*, vol. 57, pp. 2670-2682, (2014).

Lieberman, et al., "ITI-007 for the Treatment of Schizophrenia: A 4-Week Randomized, Double-Blind, Controlled Trial," *Biol. Psychiatry*, vol. 79, No. 12, pp. 952-961, (2015).

Lin, et al., "Dosage and Duration of Antipsychotic Treatment in Demented Outpatients with Agitation or Psychosis," *Journal of the Formosan Medical Association*, vol. 114, pp. 147-153, (2015).

Lipschitz, et al., "Childhood Posttraumatic Stress Disorder: A Review of Neurobiologic Sequelae," *Psychiatric Annals Journal*, vol. 28, No. 8, pp. 452-457, (1998).

Liriano et al., "Ketamine as treatment for post-traumatic stress disorder: a review." Drugs in Context, vol. 8, 7 pages (2019).

Lopez, et al., "Psychiatric Symptoms Vary with the Severity of Dementia in Probably Alzheimer's Disease," *J. Neuropsychiatry Clin. Neurosc.*, vol. 15, No. 3, pp. 346-353, (2003).

Louie, et al., "Palladium-Catalyzed Synthesis of Arylamines from Aryl Halides, Mechanistic Studies lead to Coupling in the Absence of Tin Reagents," *Tetrahedron Letters*, vol. 36, No. 21, pp. 3609-3612, (1995).

Lounkine, et al., "Formal Concept Analysis for the Identification of Molecular Fragment Combinations Specific for Active and Highly Potent Compounds," *J. Med. Chem.*, vol. 51, No. 17, pp. 5342-5348, (2008).

Madhusoodanan, et al., "Pharmacological Management of Behavioral Symptoms Associated with Dementia," *World J. Psychiatr.*, vol. 4, No. 4, pp. 72-79, (2014).

Makadia et al., "Poly Lactic-co-Glycolic Acid (PLGA) as Biodegradable Controlled Drug Delivery Carrier," *Polymers (Basel)*, vol. 3, No. 3, pp. 1377-1397, (2011).

March, et al., *Advanced Organic Chemistry; Reactions, Mechanisms and Structures*, Fourth Edition, pp. 910-911, (1992).

Marcoux, et al., "A General Copper-catalyzed Synthesis of Diaryl Ethers," *J. Am. Chem. Soc.*, vol. 119, pp. 10539-10540, (1997).

Marek et al. Synergistic Action of 5-HT2A Antagonists and Selective Serotonin Reuptake Inhibitors in Neuropsychiatric Disorders. Neuropsychopharmacology, 2003. Vol. 28, pp. 402-412. (Year: 2003).

Medisorb Fact Sheet in Medisorb Microspheres Technology (Jan. 2009) at https://static.secure.website/wscfus/6472891/uploads/Medisorb.pdf (retrieved from the internet May 18, 2020) (Year: 2009).

Meeter et al., "Effect of 5-HT on Memory and the Hippocampus: Model and Data," *Neuropsychopharmacology*, vol. 31, pp. 712-720 (2006).

Minzenberg et al., "Modafinil: A Review of Neurochemical Actions and Effects on Cognition," *Neuropsychopharmacology*, vol. 33, pp. 1477-1502 (2008).

Mohamed, et al., "Pharmacotherapy of PTSD in the U.S. Department of Veterans Affairs: Diagnostic- and Symptom-guided Drug Selection," *J. Clin. Psychiatry*, vol. 69, pp. 959-965, (2008).

Morgan, et al., "Acoustic Startle in Individuals With Posttraumatic Stress Disorder," *Psychiatric Annals Journal*, vol. 28, Issue 8, pp. 430-434, (1998).

Müller et al., "Detection of Depression in Acute Schizophrenia: Sensitivity and Specificity of 2 Standard Observer Rating Scales," *Can J Psychiatry*, vol. 51, No. 6, pp. 387-392, (2006).

Mulrooney, et al., "Recent Developments in Copper-catalyzed N-Arylation with Aryl Halides," Essay—University of Pennsylvania, (2004).

Murakami, et al., "Fischer Indolization of Ethyl Pyruvate 2-[2-(Trifluoromethyl) phenyl]-phenylhydrazone and New Insight into the Mechanism of the Goldberg Reaction," *Chem. Pharm. Bull*, vol. 43, No. 8, pp. 1281-1286, (1995).

Nagai, et al., "Synthesis of 2,3,4,4a,5,9b-hexahydro-1H-pyrido[4,3-b] indole Derivatives and Their Central Nervous System Activities," *Journal of Medicinal Chemistry*, vol. 22, No. 6, pp. 677-683, (1979).

Newman, et al., "Solid-state Analysis of the Active Pharmaceutical Ingredient in Drug Products," *Drug Discovery Today*, vol. 8, No. 19, pp. 898-903, (2003).

Noble et al., "The Opioid Receptors as Targets for Drug Abuse Medication," *British Journal of Pharmacology*, vol. 172, pp. 3964-3979, (2015); DOI: 10.1111/bph.13190.

Nihon rounen igaku zasshi, vol. 48, No. 3, pp. 195-204, (2011 nen). Partial English translation only, 2 pages.

O'Gorman, et al., "Lumateperone (ITI-007): A Novel Investigational Agent with Broad Therapeutic Potential Across Multiple Neuropsychiatric Disorders," Poster p. 1.g.038, European College of Neuropsychopharmacology (ECNP) Congress (2017).

O'Hara et al., "Serotonin Transporter Polymorphism, Memory, and Hippocampal Volume in the Elderly: Association and Interaction with Cortisol," Mol. Psychiatry, vol. 12, No. 6, 24 pages (2007).

Olivier et al., "Serotonin transporter deficiency in rats contribute to impaired object memory," *Genes, Brain and Behavior*, vol. 8, pp. 829-834 (2009).

Palanisamy, M. et al., "Cellulose-Based Matrix Microspheres of Prednisolone Inclusion Complex; Preparation and Characterization." American Association of Pharmaceutical Scientists PharmSciTech, vol. 12, No. 1, pp. 388-400, (2011).

Perlis et al., "Clinical Features of Bipolar Depression Versus Major Depressive Disorder in Large Multicenter Trials", *Am J Psychiatry*, vol. 163, vol. 2, p. 225-231, (2006).

Pieniaszek, et al., "Moricizine Bioavailability via Simultaneous Dual, Stable Isotope Administration: Bioequivalence Implications," *J. Clin. Pharmacol.*, vol. 39, pp. 817-825, (1999).

Pine et al., "Dopamine, Time, and Impulsivity in Humans," *The Journal of Neuroscience*, vol. 30, No. 26, pp. 8888-8896, (2010).

Pond, et al., "Stereospecific Reduction of Haloperidol in Human Tissues," *Biochemical Pharmacology*, vol. 44, No. 5, pp. 867-871, (1992).

"Protection for the Amino Group," *Protective Groups in Organic Synthesis, Third Edition*, John Wiley & Sons, Inc., pp. 494-505, (1999).

Pubchem, OPEN Chemistry Database, Compound Summary for CID-22036753, pp. 4, (2007), 12 pages.

Puig et al., "Serotonin and Prefrontal Cortex Function: Neurons, Networks, and Circuits," *Mol. Neurobiol.*, vol. 44, No. 3, 26 pages (2011).

Rackova, et al., "Free Radical Scavenging and Antioxidant Activities of Substituted Hexahydropyridoindoles. Quantitative Structure-Activity Relationships." *Journal of Medicinal Chemistry*, vol. 49, No. 8, pp. 2543-2548, (2006).

Rainer, M.K., "Risperidone Long-acting Injection: A Review of its Long Term Safety and Efficacy," *Neuropsychiatric Disease and Treatment*, vol. 4, No. 5, pp. 919-927, (2008).

Ramaswamy et al., "Failed Efficacy of Ziprasidone in the Treatment of Post-Traumatic Stress Disorder," *Contemporary Clinical Trials Communications*, vol. 2, pp. 1-5, (2016).

Reynolds et al., "Longitudinal Change in Memory Performance Associated with HTR2A Polymorphism," *Neurobiology of Aging*, vol. 27, pp. 150-154, (2006).

RYE (Sleep Disorders and Parkinson's Disease, 2000, accessed online http://www.waparkinsons.org/edu_research/articles/Sleep_Disorders.html), 2 pages.

Sadighi, et al., "A Highly Active Palladium Catalyst System for the Arylation of Anilines," *Tetrahedron Letters*, vol. 39, pp. 5327-5330, (1998).

Satlin, et al., "ITI-007 (Lumateperone) for the Treatment of Agitation in Patients with Dementia, including Alzheimer's Disease," Alzheimer's & Dementia 14(7) (Suppl.): P678-79 (2018) (Alzheimer's Assoc. International Conference 2018, summary of Poster P2-032).

Satlin, et al., "ITI-007 (Lumateperone) for the Treatment of Agitation in Patients with Dementia, including Alzheimer's Disease," Poster P2-032, Alzheimer's Assoc. International Conference 2018 (2018).

Savjani, et al., "Drug Solubility: Importance and Enhancement Techniques," *International Scholarly Research Network Pharmaceutics*, vol. 2012, pp. 1-10, (2012).

(56) References Cited

OTHER PUBLICATIONS

Schennach et al., "What Are Residual Symptoms in Schizophrenia Spectrum Disorder? Clinical Description and 1-year Persistence Within a Naturalistic Trial," *Eur. Arch. Psychiatry Clin. Neurosci.*, vol. 265, pp. 107-116, (2015); DOI: 10.1007/s00406-014-0528-2.
"Securities," Bennett v. Alkermes, Inc., at http://securities.stanford.edu/filings-documents/1029/ALKS03-01/20031029_r01c_0312091.pdf (retrieved from the internet on Jun. 13, 2017), (2003).
Seishinkei Shi, vol. 110, No. 7, pp. 557-584, (2008). Partial English translation only.
Semla et al., "Off-Label Prescribing of Second-Generation Antipsychotics to Elderly Veterans with Posttraumatic Stress Disorder and Dementia," *J. Am. Geriatr. Soc.*, vol. 65, No. 8, pp. 1789-1795, (2017); DOI: 10.1111/jgs.14897.
Sigel, et al., "Tenary Complexes in Solution," *Inorganic Chemistry*, vol. 13, No. 2, pp. 462-465, (1974).
Singhal, et al., "Drug Polymorphism and Dosage Form Design: A Practical Perspective," *Advanced Drug Delivery Reviews*, vol. 56, pp. 335-347, (2004).
Skoog, et al., *Principles of Instrumental Analysis*, Fourth Edition, pp. 577, (1992).
Smith, et al., "Oxford Dictionary of Biochemistry and Molecular Biology", *Oxford University Press*, pp. 145, (1997).
Snyder, et al., "Functional Profile of a Novel Modulator of Serotonin, Dopamine, and Glutamate Neurotransmission," *Psychopharmacology*, vol. 232, pp. 605-621, (2015); Published online Aug. 2014, DOI 10.1007/s00213-014-3704-1.
Southwick, et al., "Neuroendocrine Alterations in Posttraumatic Stress Disorder," *Psychiatric Annals Journal*, vol. 28, No. 8, pp. 436-442, (1998).
Sugahara, et al., "A Facile Copper-Catalyzed Ullman Condensation: N-Arylation of Heterocyclic Compounds Containing an—NHCO— Moiety," *Chem. Pharm. Bull.*, vol. 45, No. 4, pp. 719-721, (1997).
Suzuki et al., "Comparison of Nicotinamide, Ethyluirea and Polyethylene Glycol as Carriers for Nifedipine Solid Dirperssion Systems." *Chemical and Pharmaceutical Bulletin*, vol. 45, No. 10, pp. 1688-1693, (1997).
Taragano, et al., "A Double-Blind, Randomized, Fixed-Dose Trial of Fluoxetine vs. Amitriptyline in the Treatment of Major Depression Complicating Alzheimer's Disease," *Psychosomatics*, vol. 38, No. 3, pp. 246-252, (1997).
Tariot, et al., "Memantine Treatment in Patients with Moderate to Severe Alzheimer Disease Already Receiving Donepezil: A Randomized Controlled Trail," *JAMA*, vol. 291, No. 3, pp. 317-324, (2004).
Timmins, G.S., "Deuterated drugs: where are we now?" Expert Opinion on Therapeutic Patents, 1-9 (2014).
Tohen et al., "Efficacy of Olanzapine and Olanzapine-Fluoxetine Combination in the Treatment of Bipolar I Depression," Arch Gen Psychiatry, vol. 60, pp. 1079-1088, (2003).
Tonn, et al., "Simultaneous Analysis of Diphenhydramine and a Stable Isotope Analog ($^2H_{10}$)Diphenhydramine Using Capillary Gas Chromatography with Mass Selective Detection in Biological Fluids from Chronically Instrumented Pregnant Ewes," *Biological Mass Spectrometry*, vol. 22, pp. 633-642, (1993).
Tung, R., "The Development of Deuterium-Containing Drugs," *Innovations in Pharmaceutical Technology*, vol. 32, pp. 1-4, (2010).
Vanover, K., et al., "ITI-007: A Novel Therapy for the Treatment of Schizophrenia and Related Psychoses," International Clinical Psychopharamcology, vol. 26, e56, 1 page, (2011).
Vanover, et al., "A Novel Approach to Address an Unmet Need in the Treatment of Schizophrenia and Depression: Lumateperone, an Innovative Modulator of Dopamine, Serotonin, and Glutamate," Abstract presented at the American Society of Clinical Psychopharmacology (ASCP) Annual Meeting; May 29-Jun. 1, 2018; Miami, FL.
Vanover, et al., "Dopamine D2 receptor occupancy of lumateperone (ITI-007): a Positron Emission Tomography Study in patients with schizophrenia," Neuropsychopharmacology 44:598-605, (2019).
Vloeberghs et al., "Altered Circadian Locomotor Activity in APP23 Mice: A Model for BPSD Disturbances," *European Journal of Neuroscience*, vol. 20, pp. 2757-2766, (2004); DOI: 10.1111/j.1460-9568.2004.03755.x.
Vyas et al., "An Evaluation of Lumateperone Tosylate for the Treatment of Schizophrenia," *Expert Opinion on Pharmacotherapy*, vol. 21, No. 2, pp. 139-145, (2020); https://doi.org/10.1080/14656566.2019.1695778.
Wagaw, et al., "A Palladium-Catalyzed Method for the Preparation of Indoles Via the Fischer Indole Synthesis," *Journal of the American Chemical Society*, vol. 121, No. 44, pp. 10251-10263, (1999).
Warner-Schmidt et al., "Antidepressant Effects of Selective Serotonin Reuptake Inhibitors (SSRIs) are Attenuated by Antiinflammatory Drugs in Mice and Humans," *PNAS*, vol. 108, No. 22, pp. 9262-9267, (2011).
Wennogle, et al., "Activation of NMDA and AMPA Receptors by Lumateperone (ITI-007): Implications for Antidepressant Activity," Abstract presented at the 2017 Collegium Internationale Neuro-Psychopharmacologicum (CINP) Thematic Meeting: Treatment Resistant Depression; Jul. 20-22, 2017; Prague.
Weschules, et al., "Acetylcholinesterase Inhibitor and N-Methyl-D-Aspartic Acid Receptor Antagonist Use among Hospice Enrollees with a Primary Diagnosis of Dementia," *Journal of Palliative Medicine*, vol. 11, No. 5, pp. 738-745, (2008).
Wiese, M., "DSC Detection of Polymorphism in Pharmaceutical Anhydrous Dexamethasone Acetate," *TA Instruments*, TA 302, pp. 1-4, (2002).
Wolen, R. L., "The Application of Stable Isotopes to Studies of Drug Bioavailability and Bioequivalence," *J. Clin. Pharmacol.*, vol. 26, pp. 419-424, (1986).
Wolfe, et al., "An Improved Catalyst System for Aromatic Carbonnitrogen Bond Formation: The Possible Involvement of Bis(Phosphine) Palladium Complexes as Key Intermediates," *J. Am. Chem. Soc.*, vol. 118, pp. 7215-7216, (1996).
Wolfe, et al., "Intramolecular Palladium-Catalyzed Aryl Amination and Aryl Amidation," *Tetrahedron*, vol. 52, No. 21, pp. 7525-7546, (1996).
Wolter, et al., "Synthesis of N-Aryl Hydrazides by Copper-Catalyzed Coupling of Hydrazides with Aryl Iodides," *Organic Letters*, vol. 3, No. 23, pp. 3803-3805, (2001).
Written Opinion of the International Searching Authority for International Application No. PCT/US2013/036514 mailed Aug. 16, 2013, 4 pages.
Written Opinion of the International Searching Authority for International Application No. PCT/US2017/054962 mailed Nov. 27, 2017, 8 pages.
Yamada, et al., "A Mild Copper-mediated Intramolecular Amination of Aryl Halides," *Synlett*, No. 2, pp. 231-234, (2002).
Yang, et al., "The Development of Efficient Protocols for the Palladium-catalyzed Cyclization Reactions of Secondary Amides and Carbamates," *Organic Letters*, vol. 1, No. 1, pp. 35-37, (1999).
Yudofsky, et al., "Propranolol in the Treatment of Rage and Violent Behavior in Patients with Chronic Brain Syndromes," *Am. J. Psychiatry*, vol. 138, No. 2, pp. 218-220, (1981).
Zhang, et al., "Highly Efficient Copper-catalyzed N-arylation of Alkylamines with Aryl Iodides Using Phosphoramidite as Ligand," *Catalysis Communications*, vol. 6, pp. 784-787, (2005).
Zhang et al., "The Role of Serotonin 5-$HT_{2A}$ Receptors in Memory and Cognition," *Front. Pharmacol.*, vol. 6, No. 225, pp. 1-17, (2015); DOI: 10.3389/fphar.2015.00225.
Press Release, "Intra-Cellular Therapies Announces Additional Results from Phase I/II Clinical Trial for ITI-007 in Healthy Geriatric Subjects and Patients With Dementia," Intra-Cellular Therapies, Press Release Date: Nov. 21, 2014, (http://ir.intracellulartherapies.com/releasedetail.cfm?ReleaseID=884325), accessed on May 31, 2016.
"Study of a Novel Antipsychotic ITI-007 in Schizophrenia," Clinical Trials.gov, 6 pages, Dec. 26, 2011.

\* cited by examiner

COMPOSITIONS AND METHODS

CROSS REFERENCE TO RELATED APPLICATIONS

This application is a U.S. National Stage application under 35 U.S.C. § 371 of International Application No. PCT/US2019/048785, filed on Aug. 29, 2019, which claims priority to and the benefit of U.S. Provisional Application No. 62/724,472, filed Aug. 29, 2018, the contents of each of which is are incorporated herein by reference in its entirety their entireties.

FIELD

This disclosure relates to certain novel transdermal pharmaceutical formulations comprising substituted heterocycle fused gamma-carbolines, the manufacture of such formulations, and methods of use thereof, e.g., in the treatment of diseases or abnormal conditions involving or mediated by the 5-HT$_{2A}$ receptor, serotonin transporter (SERT), and/or dopamine D$_1$/D$_2$ receptor signaling pathways. The invention includes methods of treatment and/or prophylaxis of diseases and disorders including, but not limited to, anxiety, psychosis, schizophrenia, sleep disorders, sexual disorders, migraine, conditions associated with cephalic pain, social phobias, gastrointestinal disorders such as dysfunction of the gastrointestinal tract motility and obesity; depression (including major depressive disorder (MDD)) and mood disorders associated with psychosis or Parkinson's disease; psychosis such as schizophrenia associated with depression; bipolar disorder (e.g., bipolar depression); and other psychiatric and neurological conditions, as well as to combinations with other agents.

BACKGROUND 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (sometimes referred to as 4-((6bR,10aS)-3-methyl-2,3,6b,9,10,10a-hexahydro-1H-pyrido[3',4':4,5]pyrrolo[1,2,3-de]quinoxalin-8(7H)-yl)-1-(4-fluorophenyl)-1-butanone, or as ITI-007 or lumateperone), has the following structure:

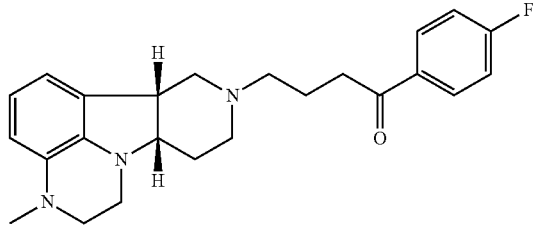

Formula I

The Compound of Formula I is a potent 5-HT$_{2A}$ receptor ligand (Ki=0.5 nM) with strong affinity for dopamine (DA) D2 receptors (K$_i$=32 nM) and the serotonin transporter (SERT) (K$_i$=26 nM, measured using 3H-imipramine binding displacement to human recombinant SERT), but negligible binding to receptors associated with cognitive and metabolic side effects of antipsychotic drugs (e.g., H1 histaminergic, 5-HT$_{2C}$, and muscarinic receptors). This compound is currently in clinical trials, i.e., for the treatment of schizophrenia, bipolar disorder and dementia including Alzheimer's disease. The Compound of Formula I, and analogs thereof, salts thereof, and methods of treatment comprising such compounds, and methods of manufacturing such compounds, have been disclosed, e.g., in U.S. Pat. Nos. 6,548,493; 7,238,690; 6,552,017; 6,713,471; 7,183,282; RE39,680; RE39,679; U.S. Patent Publications 2004/209864, 2010/113781, 2011/071080, 2011/112105, 2013/0202692, 2015/0079172, 2017/0183350; and PCT Publication WO 2017/165843 (and US 2019/0231780) and WO 2017/117514 (Tung, R. D.). The contents of each of these U.S. patents, U.S. patent Publications, and PCT Publications are hereby incorporated by reference in their entireties.

Deuterated variants of ITI-007 are generally disclosed in US 2017/0183350 and WO 2017/165843 (US 2019/0231780). The deuterated compounds are designed to slow or inhibit in vivo metabolism by substituting deuterium atoms for hydrogen atoms of ITI-007 at molecular positions which are the target of metabolic activity. The natural metabolites of ITI-007 are pharmacologically active, but with somewhat different receptor selectivity profiles. These deuterated derivatives can therefore provide modified pharmacokinetic profiles owing to altered rates or pathways of metabolism, as well as modified overall pharmacological profile due to shifting the balance between active parent species and active metabolite species.

One such deuterated compound is 1-(4-fluoro-phenyl)-4-((6bR,10aS)-2,2-d$_2$-3-methyl-2,3,6b,9,10,10a-hexahydro-1H,7H-pyrido[3',4':4,5]pyrrolo[1,2,3-de]quinoxalin-8-yl)-butan-1-one, the Compound of Formula II:

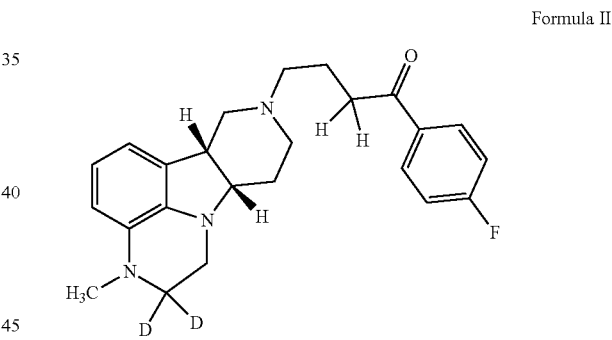

Formula II

Another such deuterated compound is 1-(4-fluoro-phenyl)-4-((6bR,10aS)-1,1,2,2-d$_4$-3-methyl-2,3,6b,9,10,10a-hexahydro-1H,7H-pyrido[3',4':4,5]pyrrolo[1,2,3-de]quinoxalin-8-yl)-butan-1-one, the Compound of Formula III:

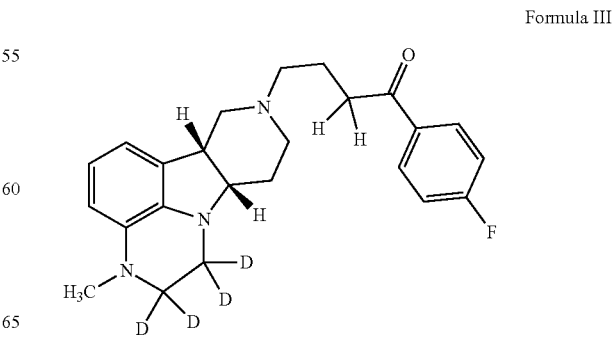

Formula III

The Compounds of Formula I, II and Formula III each undergo significant first-pass metabolism in the liver as well as significant intraluminal metabolism. For example, it has been found that the oral bioavailability of the compound of Formula I is about 5% or less. The high rate of metabolism requires the administration of higher oral doses of drug than would otherwise be needed, resulting in an increased burden on the liver, increased costs in manufacturing, difficulties in formulation and potentially higher patient-to-patient variability in dose response. There is, therefore, a need for new routes of administration that avoid first-pass hepatic metabolism and GI luminal metabolism, and which would result in correspondingly lower dosing requirements.

It has been disclosed that for a number of drugs, transdermal delivery, such as transdermal patches, transdermal gels or ointments, and transdermal sprays, are effective alternatives to traditional dosage forms such as parenteral and oral dosing. Parenteral (intravenous) dosing is very effective in avoiding first-pass and GI metabolism but is limited in its usefulness because it requires administration by trained professionals, usually in a clinical environment. In contrast, transdermal delivery systems can be used to formulate drugs which can be taken by patients without professional supervision and can result in steady, long-term drug absorption with minimal first-pass metabolism.

The use of transdermal drug delivery formulations is well known, with transdermal patch formulations of scopolamine dating back to 1979. These formulations involve the transfer of active drug agent across and through the epidermal and dermal layers of the skin to reach the capillaries deep within the dermis, which is distinct from dermal drug delivery, in which a drug active is merely delivered to the skin itself. Transdermal drug delivery is a method of systemic drug administration, not local administration. Transdermal drug delivery is difficult to achieve due to the natural impermeability of the skin to foreign substances, including water. Transdermal drug delivery is thus particularly difficult for water-soluble drug substances. In contrast to transdermal drug delivery is transmucosal drug delivery, in which a drug substance is transported across a mucous membrane, including the oral mucosa, nasal mucosa, and the vaginal mucosa. Like trans-mucosal drug delivery, trans-dermal drug delivery has the distinct advantage of avoiding first-pass hepatic and GI metabolism, and it is also patient friendly as the common formulations, such as patches, can be applied by patients and replaced on an infrequent basis. Many transdermal drug delivery systems can be optimized to ensure long-term (e.g., days or weeks) of steady, stable systemic drug delivery.

Existing transdermal delivery systems include patches, gels, ointments and sprays. Examples of such delivery systems include those disclosed in U.S. Pat. No. 9,993,466 to Lee et al., U.S. Pat. No. 9,913,840 to Jain et al., U.S. Pat. No. 9,693,970 to Mo, U.S. Pat. No. 9,585,862 to Hwang et al., and U.S. Pat. No. 7,858,114 to Ito. Individual formulations must be fine-tuned to particular active pharmaceutical ingredients to ensure accuracy and reliability in delivery. Thus, while the field of transdermal drug delivery has a long history, considerable effort is required in adapting any selected transdermal delivery technology to a particular active pharmaceutical ingredient.

The use of transdermal drug delivery is particularly useful when treating patients who are or are expected to be unreliable in daily dosing with oral medications. Foremost among such patients are those with psychiatric or neurological illnesses, such as psychosis, schizophrenia and cognitive and memory disorders (e.g., dementias, such as Alzheimer's disease).

Compounds of Formula I, II and III in free base form are hydrophobic and have good lipid-solubility, but they are difficult to crystallize and tend to exist as oils. In contrast, Compounds of Formula I, II and III may exist in stable, solid crystal salt forms which are easy to handle, but are not lipid-soluble. As a result, developing a transdermal formulation of these compounds may not be an easy undertaking.

There is a need for improved pharmaceutical delivery systems for the safe, effective, reliable delivery of the Compounds for Formula I and/or the Compound of Formula II, especially for long-term treatment of patients for whom daily oral dosing is unreliable. The present disclosure provides novel transdermal formulations for the delivery of these compounds without the drawbacks of existing parenteral and oral delivery systems.

BRIEF SUMMARY

The present disclosure is directed to novel transdermal pharmaceutical formulations comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (lumateperone), as well as deuterated variants thereof, in free base, co-crystal or salt forms. Transdermal formulations include, but are not limited to patches, gels, ointments, and sprays.

Further areas of applicability of the present invention will become apparent from the detailed description provided hereinafter. It should be understood that the detailed description and specific examples, while indicating preferred embodiments of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material in free base equivalent form.

In a first embodiment, the present disclosure provides a transdermal pharmaceutical formulation (Formulation 1) comprising 1-(4-fluoro-phenyl)-4-((6bR,10aS)-3-methyl-2,3,6b,9,10,10a-hexahydro-1H,7H-pyrido[3',4':4,5]pyrrolo[1,2,3-de]quinoxalin-8-yl)-butan-1-one (Compound of Formula I), in free base, co-crystal or salt form. The present disclosure further provides the following Formulations:

1.1. Formulation 1, wherein the formulation comprises the Compound of Formula I in free base form.
1.2. Formulation 1, wherein the formulation comprises the Compound of Formula I in salt form, e.g., in pharmaceutically acceptable salt form, optionally in amorphous solid or crystal salt form; or in co-crystal form, e.g., in nicotinamide or isonicotinamide co-crystal form.
1.3. Formulation 1.2, wherein the salt form is a tosylate, oxalate, cyclamate, 4-aminosalicylate, or hydrochloride salt form, optionally, wherein said salt form is a crystal salt form.
1.4. Any preceding formulation, wherein the formulation comprises from 1 to 1000 mg of the Compound of Formula I (free base equivalent), e.g., 1 to 750 mg, 1 to 500 mg, 1 to 300 mg, 1 to 200 mg, 10 to 200 mg, 50 to 200 mg, 100 to 200 mg, 100 to 300 mg, 200 to 300 mg, 200 to 500 mg, or 500 to 1000 mg.
1.5. Any preceding formulation, wherein the formulation comprises from 1 to 100 mg of the Compound of Formula I (free base equivalent), e.g., 10 to 70 mg, or 40 to 70 mg.
1.6. Any preceding formulation, wherein the formulation comprises from 1 to 80 mg of the Compound of Formula I (free base equivalent), e.g., from 1 to 50 mg, or from to 5 to 50 mg.
1.7. Any preceding formulation, wherein the composition further comprises one or more excipients, e.g., materials which stabilize the Compound of Formula I, and/or enhance absorption into the skin of the Compound of Formula I.
1.8. Formula 1.7, wherein the one or more excipients are selected from the group consisting of solvents, solubilizers, plasticizers, surfactants, binders, humectants (e.g., polyols), antioxidants, buffering agents (e.g., acids, bases and/or salts thereof), emollients, and thickening agents (e.g., gelling agents).
1.9. Formula 1.7, wherein the one or more excipients are selected from any of the following: alcohols (ethanol, isopropanol, propanol, glycerol, propylene glycol, butylene glycol, pentylene glycol, hexylene glycol, polyethylene glycol), non-alcoholic solvents (e.g., dimethylsulfoxide, dimethylformamide, acetonitrile), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropyl methyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinylpyrrolidones, polyethylene oxide and/or polypropylene oxide polymers and copolymers (e.g., poloxamers, such as poloxamer 188), polyacrylate polymers (e.g., carbopols), polyamide polymers, sugars and sugar alcohols (e.g., dextrose, lactose, galactose, glucose, ribose, sucrose, trehalose, mannitol, maltitol, lactitol, sorbitol, xylitol, erythritol, galactitol, inositol) polypeptides/proteins, amino acids, inorganic or organic acids (e.g., citric acid, lactic acid, malic acid, mandelic acid, tropic acid, glycolic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids) and esters (e.g., methyl or ethyl esters, or fatty acid esters), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzenesulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine, or amine oxides, such as dimethyldodecylamine oxide and myristamine oxide), nonionic surfactants (e.g., fatty alcohol ethoxylates (e.g., polyethylene glycol polydodecyl ethers)), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), fatty acid esters (e.g., lauryl lactate, isopropyl myristate, oleyl oleate, methyl laurate, isopropyl palmitate, ethyl oleate), fatty alcohols (e.g., dodecanol, octyldecanol, lauryl alcohol), and antioxidants (e.g., ascorbic acid, citric acid, ascorbyl palmitate, sodium metabisulfite, BHT, BHA, TBHQ, propyl gallate, beta-carotene, tocopherols, tocotrienols).
1.10. Any of Formulations 1.7 to 1.9, wherein any one or more of said excipients are present in an amount of 0.1 to 80% by weight of the formulation, e.g., 0.1 to 60%, or 0.1 to 40%, or 0.1 to 20%, or 0.1 to 15% or 0.1 to 10%.
1.11. Any preceding formulation, wherein the formulation comprises an adhesive polymer, optionally in an amount from 25-80% by weight.
1.12. Formulation 1.11, wherein the adhesive polymer comprises a polymer selected from the group consisting of acrylate polymers or co-polymers (e.g., polymers in which at least one monomeric unit is an acrylic acid or ester, and in which one or more other monomeric units may be a non-acrylate monomer, e.g., a vinyl monomer), polyvinylpyrrolidones (e.g., linear or cross-linked), copolymers of maleic acid or a maleic ester with a vinyl ether (e.g., co-polymer of maleic acid or anhydride with methyl vinyl ether), cellulose derivatives (e.g., carboxymethyl cellulose), silicone polymers (e.g., dimethylsilicone), and mixtures thereof, such as, a mixture of a polyacrylate polymer and a silicone polymer.
1.13. Any preceding formulation, wherein the formulation is an ointment.
1.14. Any of formulations 1 or 1.1 to 1.11, wherein the formulation is a spray.
1.15. Any of formulations 1 or 1.1 to 1.11, wherein the formulation is a gel.
1.16. Any of formulations 1 or 1.1 to 1.11, wherein the formulation is comprised in a patch, e.g., an adhesive patch.
1.17. Formulation 1.16, wherein the patch comprises at least one drug reservoir layer and wherein the formulation is the drug reservoir layer.
1.18. Formulation 1.17, wherein the drug reservoir layer is adhesive.
1.19. Any preceding formulation wherein the Compound of Formula I is incorporated into the formulation as microparticles (e.g., particles having an average diameter of less than 50 μm, less than 30 μm, less than 10 μm, or less than 5 μm, or less than 1 μm).
1.20. Any preceding formulation, wherein the formulation further comprises the Compound of Formula II or the Compound of Formula III or a combination thereof.

1.21. Any preceding formulation, wherein the formulation comprises the Compound of Formula I in tosylate salt form, e.g., in mono-tosylate salt form or di-tosylate salt form, or a mixture thereof.

1.22. Formulation 1.21, wherein the formulation further comprises toluenesulfonic acid, e.g., wherein the formulation comprises the Compound of Formula I in tosylate salt form and toluenesulfonic acid in a ratio of 1:3 to 3:1, or 1:2 to 2:1 or 1:1.5 to 1.5:1, or about 1:1.

1.23. Any preceding formulation, wherein the Compound of Formula I is enriched in deuterium at one or more hydrogen atom positions, for example, wherein at any one or more hydrogen atom positions there is substantially greater than the natural level of incorporation of deuterium at such positions of the structure (e.g., greater than 0.1%, or greater than 0.5%, or greater than 1%, or greater than 5%).

1.24. Formulation 1.23, wherein the Compound of Formula I has greater than 50% incorporation of deuterium at any one or more hydrogen atom positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

1.25. Any of formulations 1 or 1.1 to 1.24, wherein all hydrogen atom positions of the Compound of Formula I are non-enriched in deuterium (i.e., every hydrogen atom position contains the natural abundance of deuterium or less than 0.1% deuterium).

1.26. Any of formulations 1 or 1.1 to 1.25, wherein the formulation systemically delivers a mean daily dose of the compound of Formula I of 0.1 to 5.0 mg per day (free base equivalent), e.g., 0.5 to 2.0 mg per day, or 0.1 to 0.5 mg per day, or 1.0 to 2.0 mg per day, or about 1.8 mg per day.

1.27. Any of formulations 1 or 1.1 to 1.26, wherein the formulation delivers the compound of Formula I at a rate sufficient to maintain a steady state maximum plasma concentration of the compound of Formula I (free base) of 5 to 50 ng/mL, e.g., 10 to 40 ng/mL, or 20 to 40 ng/mL (e.g., about 30 ng/mL) and/or sufficient to maintain a steady state 24-hour mean plasma concentration area under the curve (AUC) of the compound of Formula I (free base) of 5 to 100 ng-hr/mL, e.g., 20 to 90 ng-hr/mL, or 40 to 90 ng-hr/mL, or 70 to 90 ng hr/mL (e.g., about 80 ng-hr/mL).

In a second embodiment, the present disclosure provides a transdermal pharmaceutical formulation (Formulation 2) comprising 1-(4-fluoro-phenyl)-4-((6bR,10aS)-2,2-d$_2$-3-methyl-2,3,6b,9,10,10a-hexahydro-1H,7H-pyrido[3',4':4,5]pyrrolo[1,2,3-de]quinoxalin-8-yl)-butan-1-one (Compound of Formula II), in free base, co-crystal or salt form. The present disclosure further provides the following Formulations:

2.1. Formulation 2, wherein the formulation comprises the Compound of Formula II in free base form.

2.2. Formulation 2, wherein the formulation comprises the Compound of Formula II in salt form, e.g., in pharmaceutically acceptable salt form, optionally in amorphous solid or crystal salt form; or in co-crystal form, e.g., in nicotinamide or isonicotinamide co-crystal form.

2.3. Formulation 2.2, wherein the salt form is a tosylate, oxalate, cyclamate, 4-aminosalicylate, or hydrochloride salt form, optionally, wherein said salt form is a crystal salt form.

2.4. Any preceding formulation, wherein the formulation comprises from 1 to 1000 mg of the Compound of Formula II (free base equivalent), e.g., 1 to 750 mg, 1 to 500 mg, 1 to 300 mg, 1 to 200 mg, 10 to 200 mg, 50 to 200 mg, 100 to 200 mg, 100 to 300 mg, 200 to 300 mg, 200 to 500 mg, or 500 to 1000 mg.

2.5. Any preceding formulation, wherein the formulation comprises from 1 to 100 mg of the Compound of Formula II (free base equivalent), e.g., 10 to 70 mg, or 40 to 70 mg.

2.6. Any preceding formulation, wherein the formulation comprises from 1 to 80 mg of the Compound of Formula II (free base equivalent), e.g., from 1 to 50 mg, or from to 5 to 50 mg.

2.7. Any preceding formulation, wherein the composition further comprises one or more excipients, e.g., materials which stabilize the Compound of Formula II, and/or enhance absorption into the skin of the Compound of Formula II.

2.8. Formula 2.7, wherein the one or more excipients are selected from the group consisting of solvents, solubilizers, plasticizers, surfactants, binders, humectants (e.g., polyols), antioxidants, buffering agents (e.g., acids, bases and/or salts thereof), emollients, and thickening agents (e.g., gelling agents).

2.9. Formula 2.7, wherein the one or more excipients are selected from any of the following: alcohols (ethanol, isopropanol, propanol, glycerol, propylene glycol, butylene glycol, pentylene glycol, hexylene glycol, polyethylene glycol), non-alcoholic solvents (e.g., dimethylsulfoxide, dimethylformamide, acetonitrile), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropyl methyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinylpyrrolidones, polyethylene oxide and/or polypropylene oxide polymers and copolymers (e.g., poloxamers, such as poloxamer 188), polyacrylate polymers (e.g., carbopols), polyamide polymers), sugars and sugar alcohols (e.g., dextrose, lactose, galactose, glucose, ribose, sucrose, trehalose, mannitol, maltitol, lactitol, sorbitol, xylitol, erythritol, galactitol, inositol) polypeptides/proteins, amino acids, inorganic or organic acids (e.g., citric acid, lactic acid, malic acid, mandelic acid, tropic acid, glycolic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids) and esters (e.g., methyl or ethyl esters, or fatty acid esters), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzenesulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine, or amine oxides, such as dimethyldodecylamine oxide and myristamine oxide), nonionic surfactants (e.g., fatty alcohol ethoxylates (e.g., polyethylene glycol polydodecyl ethers), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), fatty acid esters (e.g., lauryl lactate, isopropyl myristate, oleyl oleate, methyl laurate, isopropyl palmitate, ethyl oleate), fatty alcohols (e.g., dodecanol, octyldecanol, lauryl alcohol), and antioxidants (e.g., ascorbic acid, citric acid, ascorbyl palmitate, sodium metabisulfite, BHT, BHA, TBHQ, propyl gallate, beta-carotene, tocopherols, tocotrienols).

2.10. Any of Formulations 2.7 to 2.9, wherein any one or more of said excipients are present in an amount of 0.1 to 80% by weight of the formulation, e.g., 0.1 to 60%, or 0.1 to 40%, or 0.1 to 20%, or 0.1 to 15% or 0.1 to 10%.

2.11. Any preceding formulation, wherein the formulation comprises an adhesive polymer, optionally in an amount from 25-80% by weight.

2.12. Formulation 2.11, wherein the adhesive polymer comprises a polymer selected from the group consisting of acrylate polymers or co-polymers (e.g., polymers in which at least one monomeric unit is an acrylic acid or ester, and in which one or more other monomeric units may be a non-acrylate monomer, e.g., a vinyl monomer), polyvinylpyrrolidones (e.g., linear or cross-linked), copolymers of maleic acid or a maleic ester with a vinyl ether (e.g., co-polymer of maleic acid or anhydride with methyl vinyl ether), cellulose derivatives (e.g., carboxymethyl cellulose), silicone polymers (e.g., dimethylsilicone), and mixtures thereof, such as, a mixture of a polyacrylate polymer and a silicone polymer.

2.13. Any preceding formulation, wherein the formulation is an ointment.

2.14. Any of formulations 2 or 2.1 to 2.11, wherein the formulation is a spray.

2.15. Any of formulations 2 or 2.1 to 2.11, wherein the formulation is a gel.

2.16. Any of formulations 2 or 2.1 to 2.11, wherein the formulation is comprised in a patch, e.g., an adhesive patch.

2.17. Formulation 2.16, wherein the patch comprises at least one drug reservoir layer and wherein the formulation is the drug reservoir layer.

2.18. Formulation 2.17, wherein the drug reservoir layer is adhesive.

2.19. Any preceding formulation wherein the Compound of Formula II is incorporated into the formulation as microparticles (e.g., particles having an average diameter of less than 50 µm, less than 30 µm, less than 10 µm, or less than 5 µm, or less than 1 µm).

2.20. Any preceding formulation, wherein the formulation further comprises the Compound of Formula I or the Compound of Formula III or a combination thereof.

2.21. Any preceding formulation, wherein the formulation comprises the Compound of Formula II in tosylate salt form, e.g., in mono-tosylate salt form or di-tosylate salt form, or a mixture thereof.

2.22. Formulation 2.21, wherein the formulation further comprises toluenesulfonic acid, e.g., wherein the formulation comprises the Compound of Formula II in tosylate salt form and toluenesulfonic acid in a ratio of 1:3 to 3:1, or 1:2 to 2:1 or 1:1.5 to 1.5:1, or about 1:1.

2.23. Any preceding formulation, wherein the Compound of Formula II is enriched in deuterium at one or more hydrogen atom positions, for example, wherein at any one or more hydrogen atom positions there is substantially greater than the natural level of incorporation of deuterium at such positions of the structure (e.g., greater than 0.1%, or greater than 0.5%, or greater than 1%, or greater than 5%).

2.24. Formulation 2.23, wherein the Compound of Formula II has greater than 50% incorporation of deuterium at any one or more hydrogen atom positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

2.25. Any of formulations 2 or 2.1 to 2.24, wherein all hydrogen atom positions of the Compound of Formula II are non-enriched in deuterium (i.e., every hydrogen atom position contains the natural abundance of deuterium or less than 0.1% deuterium; 2.26. Any of formulations 2 or 2.1 to 2.25, wherein the formulation systemically delivers a mean daily dose of the compound of Formula II of 0.1 to 5.0 mg per day (free base equivalent), e.g., 0.5 to 2.0 mg per day, or 0.1 to 0.5 mg per day, or 1.0 to 2.0 mg per day, or about 1.8 mg per day.

2.27. Any of formulations 2 or 2.1 to 2.26, wherein the formulation delivers the compound of Formula II at a rate sufficient to maintain a steady state maximum plasma concentration of the compound of Formula II (free base) of 5 to 50 ng/mL, e.g., 10 to 40 ng/mL, or 20 to 40 ng/mL (e.g., about 30 ng/mL) and/or sufficient to maintain a steady state 24-hour mean plasma concentration area under the curve (AUC) of the compound of Formula II (free base) of 5 to 100 ng-hr/mL, e.g., 20 to 90 ng-hr/mL, or 40 to 90 ng-hr/mL, or 70 to 90 ng hr/mL (e.g., about 80 ng-hr/mL).

In a third embodiment, the present disclosure provides a transdermal pharmaceutical formulation (Formulation 3) comprising 1-(4-fluoro-phenyl)-4-((6bR,10aS)-1,1,2,2-d$_4$-3-methyl-2,3,6b,9,10,10a-hexahydro-1H,7H-pyrido[3',4':4,5]pyrrolo[1,2,3-de]quinoxalin-8-yl)-butan-1-one (Compound of Formula III), in free base, co-crystal or salt form. The present disclosure further provides the following Formulations:

3.1. Formulation 3, wherein the formulation comprises the Compound of Formula III in free base form.

3.2. Formulation 3, wherein the formulation comprises the Compound of Formula III in salt form, e.g., in pharmaceutically acceptable salt form, optionally in amorphous solid or crystal salt form; or in co-crystal form, e.g., in nicotinamide or isonicotinamide co-crystal form.

3.3. Formulation 3.2, wherein the salt form is a tosylate, oxalate, cyclamate, 4-aminosalicylate, or hydrochloride salt form, optionally, wherein said salt form is a crystal salt form.

3.4. Any preceding formulation, wherein the formulation comprises from 1 to 1000 mg of the Compound of Formula III (free base equivalent), e.g., 1 to 750 mg, 1 to 500 mg, 1 to 300 mg, 1 to 200 mg, 10 to 200 mg, 50 to 200 mg, 100 to 200 mg, 100 to 300 mg, 200 to 300 mg, 200 to 500 mg, or 500 to 1000 mg.

3.5. Any preceding formulation, wherein the formulation comprises from 1 to 100 mg of the Compound of Formula III (free base equivalent), e.g., 10 to 70 mg, or 40 to 70 mg.

3.6. Any preceding formulation, wherein the formulation comprises from 1 to 80 mg of the Compound of Formula III (free base equivalent), e.g., from 1 to 50 mg, or from to 5 to 50 mg.

3.7. Any preceding formulation, wherein the composition further comprises one or more excipients, e.g., materials which stabilize the Compound of Formula III, and/or enhance absorption into the skin of the Compound of Formula III.

3.8. Formula 3.7, wherein the one or more excipients are selected from the group consisting of solvents, solubilizers, plasticizers, surfactants, binders, humectants (e.g., polyols), antioxidants, buffering agents (e.g., acids, bases and/or salts thereof), emollients, and thickening agents (e.g., gelling agents).

3.9. Formula 3.7, wherein the one or more excipients are selected from any of the following: alcohols (ethanol, isopropanol, propanol, glycerol, propylene glycol, butylene glycol, pentylene glycol, hexylene glycol, polyethylene glycol), non-alcoholic solvents (e.g., dimethylsulfoxide, dimethylformamide, acetonitrile), gums (e.g., acacia, guar, agar, xanthan, tragacanth, karaya, gellan), polysaccharides and polysaccharide derivatives (e.g., starches, dextrans, pectins, alginates, carrageenans, cellulose, cellulose derivatives (e.g., carboxymethyl cellulose, methylcellulose, hydroxyalkyl celluloses (e.g., hydroxyethyl cellulose, hydroxypropyl cellulose, hydroxypropyl methyl cellulose)), gelatins including non-gelling and gelling types (e.g., mammalian gelatins such as bovine gelatin, porcine gelatins, avian gelatins, fish gelatins (e.g., mixed high molecular weight and low molecular weight gelatins), synthetic polymers (e.g., polyvinylpyrrolidones, polyethylene oxide and/or polypropylene oxide polymers and copolymers (e.g., poloxamers, such as poloxamer 188), polyacrylate polymers (e.g., carbopols), polyamide polymers), sugars and sugar alcohols (e.g., dextrose, lactose, galactose, glucose, ribose, sucrose, trehalose, mannitol, maltitol, lactitol, sorbitol, xylitol, erythritol, galactitol, inositol) polypeptides/proteins, amino acids, inorganic or organic acids (e.g., citric acid, lactic acid, malic acid, mandelic acid, tropic acid, glycolic acid, gluconic acid, benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid) and their salts (e.g., sodium, potassium, calcium, magnesium, lithium, ammonium salts of aforementioned acids) and esters (e.g., methyl or ethyl esters, or fatty acid esters), inorganic or organic bases (e.g., alkali metal or alkaline earth metal carbonates, bicarbonates, hydroxide, oxides), anionic surfactants (e.g., sodium lauryl sulfate, sodium laureth sulfate, sodium dodecylbenzenesulfonate, sodium lauroyl sarcosinate, sodium stearate), cationic surfactants (e.g., benzalkonium halides, cetylpyridinium halides, cetrimonium halides, benzethonium halides), zwitterionic surfactants (e.g., cocamidoalkyl betaines, such as cocamidopropyl betaine, or amine oxides, such as dimethyldodecylamine oxide and myristamine oxide), nonionic surfactants (e.g., fatty alcohol ethoxylates (e.g., polyethylene glycol polydodecyl ethers), sorbitan esters (e.g., sorbitan monolaurate, sorbitan monooleate, sorbitan monopalmitate, sorbitan monostearate, sorbitan tristearate), polyethoxylated sorbitan esters (e.g., polysorbate 20, polysorbate 40, polysorbate 60, polysorbate 80), fatty acid esters (e.g., lauryl lactate, isopropyl myristate, oleyl oleate, methyl laurate, isopropyl palmitate, ethyl oleate), fatty alcohols (e.g., dodecanol, octyldecanol, lauryl alcohol), and antioxidants (e.g., ascorbic acid, citric acid, ascorbyl palmitate, sodium metabisulfite, BHT, BHA, TBHQ, propyl gallate, beta-carotene, tocopherols, tocotrienols).

3.10. Any of Formulations 3.7 to 3.9, wherein any one or more of said excipients are present in an amount of 0.1 to 80% by weight of the formulation, e.g., 0.1 to 60%, or 0.1 to 40%, or 0.1 to 20%, or 0.1 to 15% or 0.1 to 10%.

3.11. Any preceding formulation, wherein the formulation comprises an adhesive polymer, optionally in an amount from 25-80% by weight.

3.12. Formulation 3.11, wherein the adhesive polymer comprises a polymer selected from the group consisting of acrylate polymers or co-polymers (e.g., polymers in which at least one monomeric unit is an acrylic acid or ester, and in which one or more other monomeric units may be a non-acrylate monomer, e.g., a vinyl monomer); polyvinylpyrrolidones (e.g., linear or cross-linked), copolymers of maleic acid or a maleic ester with a vinyl ether (e.g., co-polymer of maleic acid or anhydride with methyl vinyl ether), cellulose derivatives (e.g., carboxymethyl cellulose), silicone polymers (e.g., dimethylsilicone), and mixtures thereof, such as, a mixture of a polyacrylate polymer and a silicone polymer.

3.13. Any preceding formulation, wherein the formulation is an ointment.

3.14. Any of formulations 3 or 3.1 to 3.11, wherein the formulation is a spray.

3.15. Any of formulations 3 or 3.1 to 3.11, wherein the formulation is a gel.

3.16. Any of formulations 3 or 3.1 to 3.11, wherein the formulation is comprised in a patch, e.g., an adhesive patch.

3.17. Formulation 3.16, wherein the patch comprises at least one drug reservoir layer and wherein the formulation is the drug reservoir layer.

3.18. Formulation 3.17, wherein the drug reservoir layer is adhesive.

3.19. Any preceding formulation wherein the Compound of Formula III is incorporated into the formulation as microparticles (e.g., particles having an average diameter of less than 50 µm, less than 30 µm, less than 10 µm, or less than 5 µm, or less than 1 µm).

3.20. Any preceding formulation, wherein the formulation further comprises the Compound of Formula I or the Compound of Formula II or a combination thereof.

3.21. Any preceding formulation, wherein the formulation comprises the Compound of Formula III in tosylate salt form, e.g., in mono-tosylate salt form or di-tosylate salt form, or a mixture thereof.

3.22. Formulation 3.21, wherein the formulation further comprises toluenesulfonic acid, e.g., wherein the formulation comprises the Compound of Formula III in tosylate salt form and toluenesulfonic acid in a ratio of 1:3 to 3:1, or 1:2 to 2:1 or 1:1.5 to 1.5:1, or about 1:1.

3.23. Any preceding formulation, wherein the Compound of Formula III is enriched in deuterium at one or more hydrogen atom positions, for example, wherein at any one or more hydrogen atom positions there is substantially greater than the natural level of incorporation of deuterium at such positions of the structure (e.g., greater than 0.1%, or greater than 0.5%, or greater than 1%, or greater than 5%).

3.24. Formulation 3.23, wherein the Compound of Formula III has greater than 50% incorporation of deuterium at any one or more hydrogen atom positions of the structure (i.e., greater than 50 atom % D), e.g., greater than 60%, or greater than 70%, or greater than 80%, or greater than 90% or greater than 95%, or greater than 96%, or greater than 97%, or greater than 98%, or greater than 99%.

3.25. Any of formulations 3 or 3.1 to 3.24, wherein all hydrogen atom positions of the Compound of Formula III are non-enriched in deuterium (i.e., every hydrogen atom position contains the natural abundance of deuterium or less than 0.1% deuterium).

3.26. Any of formulations 3 or 3.1 to 3.25, wherein the formulation systemically delivers a mean daily dose of the compound of Formula III of 0.1 to 5.0 mg per day (free base equivalent), e.g., 0.5 to 2.0 mg per day, or 0.1 to 0.5 mg per day, or 1.0 to 2.0 mg per day, or about 1.8 mg per day.

3.27. Any of formulations 3 or 3.1 to 3.26, wherein the formulation delivers the compound of Formula III at a rate sufficient to maintain a steady state maximum plasma concentration of the compound of Formula III (free base) of 5 to 50 ng/mL, e.g., 10 to 40 ng/mL, or 20 to 40 ng/mL (e.g., about 30 ng/mL) and/or sufficient to maintain a steady state 24-hour mean plasma concentration area under the curve (AUC) of the compound of Formula III (free base) of 5 to 100 ng-hr/mL, e.g., 20 to 90 ng-hr/mL, or 40 to 90 ng-hr/mL, or 70 to 90 ng hr/mL (e.g., about 80 ng-hr/mL).

In a fourth embodiment, the present disclosure provides a transdermal pharmaceutical device (Device 1) comprising any of Formulation 1 et seq, Formula 2 et seq, or Formula 3 et seq. In particular embodiments, the present disclosure further provides:

1.1. Device 1, wherein the device comprises at least two layers, wherein at least one layer is a drug reservoir layer (e.g., a layer comprising the compound of Formula I, or Formula II, or Formula III), and at least one layer is a backing layer (e.g., a layer which is an inert layer and which is substantially free of and substantially impermeable to the compounds of Formula I, Formula II and Formula III).

1.2. Device 1.1, wherein the drug reservoir layer comprises or consists of Formulation 1 or any of 1.1-1.27.

1.3. Device 1.1, wherein the drug reservoir layer comprises or consists of Formulation 2 or any of 2.1-2.27.

1.4. Device 1.1, wherein the drug reservoir layer comprises or consists of Formulation 3 or any of 3.1-3.27.

1.5. Any preceding Device, wherein the drug reservoir layer comprises an adhesive polymer, as defined hereinabove, and wherein the drug reservoir layer is the skin-contacting layer of the device.

1.6. Device 1.5, wherein the drug reservoir layer comprises the adhesive polymer in an amount from 25-80% by weight, e.g., from 30-65% by weight, or from 40 to 60% by weight.

1.7. Device 1 or any of 1.1-1.4, wherein the Device further comprises a third layer, separate from the drug reservoir layer, which third layer is the skin-contacting layer and which layer comprises an adhesive polymer, as defined hereinabove, and which layer is substantially free of the compounds of Formula I, Formula II and Formula III prior to use of the device.

1.8. Device 1.7, wherein the skin-contacting layer comprises the adhesive polymer in an amount from 25-90% by weight, e.g., from 50-90% by weight, or from 65 to 90% by weight.

1.9. Device 1.7 or 1.8, wherein the device further comprises an intermediate layer disposed between the skin contact layer and the drug reservoir layer, which layer is a rate-control layer optionally comprising any of the excipients set forth hereinabove.

1.10. Device 1.9, wherein the intermediate layer is a microporous polymer layer, e.g., wherein the polymer layer comprises polyethylene, polypropylene, polyurethane, polyester, vinyl acetate polymer or copolymer, or combinations thereof.

1.11. Any preceding device, wherein the drug reservoir layer and/or the skin-contacting layer comprise one or more permeation enhancing excipients, for example, a fatty acid ester (e.g., lauryl lactate), an alcohol (e.g., propylene glycol), an amine oxide (e.g., dimethyldodecyl amine oxide), and/or a carboxylic acid (e.g., an alpha-hydroxy acid, e.g., lactic acid).

1.12. Any preceding device wherein the drug reservoir layer comprises the Compound of Formula I, or the compound of Formula II, or the compound of Formula III in free base form.

1.13. Any preceding device wherein the drug reservoir layer comprises the Compound of Formula I, or the compound of Formula II, or the compound of Formula III in pharmaceutically acceptable salt form (e.g., tosylate salt form) in admixture with at least one organic or inorganic base, e.g., in order to slowly generate the free base form of said Compound.

1.14. Any preceding device, wherein the backing layer is flexible or partially flexible.

1.15. Any preceding device, wherein the backing layer is comprised of one or more of a film, a non-woven fabric, a woven fabric, a laminate, or combinations thereof.

1.16. Any preceding device, wherein the backing layer comprises one or more polymers selected from polyesters, polyamides, polyvinylidene chloride, polyvinyl chloride, polyethylene, polypropylene, polyurethane, polyether amides, polyvinyl acetate, nylons.

1.17. Any preceding device further comprising a release liner which is at least partially in contact with the skin-contacting layer or drug reservoir layer and which protects the adhesive elements of the device prior to use and prevents migration of any components of the device out of the device prior to use.

1.18. Device 1.17, wherein the release liner is an impermeable polymer film.

1.19. Any preceding device, wherein the device comprises from 1 to 1000 mg of the Compound of Formula I or the Compound of Formula II or the Compound of Formula III (free base equivalent), e.g., 1 to 750 mg, 1 to 500 mg, 1 to 300 mg, 1 to 200 mg, 10 to 200 mg, 50 to 200 mg, 100 to 200 mg, 100 to 300 mg, 200 to 300 mg, 200 to 500 mg, or 500 to 1000 mg.

1.20. Any preceding device, wherein the device is formulated to deliver the Compound of Formula I or the Compound of Formula II or the Compound of Formula III to a patient over a period of time from 1 to 30 days, e.g., from 1 to 20 days, or from 1 to 15 days, or from 1 to 10 days, or from 1 to 7 days, or from 1 to 5 days, or from 1 to 3 days.

1.21. Any preceding device, wherein the device is formulated to deliver the Compound of Formula I or the Compound of Formula II or the Compound of Formula III to a patient at an average daily dosage of from 1 to 60 mg per day (free base equivalent), e.g., 1 to 40 mg per day, or 1 to 30 mg per day, or 1 to 20 mg per day, or 1 to 15 mg per day, or 1 to 10 mg per day.

1.22. Any preceding device, wherein the device provides an in vitro flux of the Compound of Formula I or the Compound of Formula II or the Compound of Formula III of between 10 and 500 µg/hr/cm² (free base equivalent).

1.23. Any preceding device, wherein the device systemically delivers a mean daily dose of the compound of Formula I or the Compound of Formula II or the Compound of Formula III of 0.1 to 5.0 mg per day (free base equivalent), e.g., 0.5 to 2.0 mg per day, or 0.1 to 0.5 mg per day, or 1.0 to 2.0 mg per day, or about 1.8 mg per day.

1.24. Any preceding device, wherein the device delivers the compound of Formula I or the Compound of Formula II or the Compound of Formula III at a rate sufficient to maintain a steady state maximum plasma concentration of the compound (free base) of 5 to 50 ng/mL, e.g., 10 to 40 ng/mL, or 20 to 40 ng/mL (e.g., about 30 ng/mL) and/or sufficient to maintain a steady state 24-hour mean plasma concentration area under the curve (AUC) of the compound (free base) of 5 to 100 ng-hr/mL, e.g., 20 to 90 ng-hr/mL, or 40 to 90 ng-hr/mL, or 70 to 90 ng hr/mL (e.g., about 80 ng-hr/mL).

As used herein, the term "transdermal formulation" or "transdermal delivery" does not embrace "trans-mucosal" routes of administration, such as sublingual, oral, buccal, vaginal intranasal and pulmonary. Transdermal delivery refers to the transport of a drug substance through the skin, e.g., keratinized epithelium, for absorption in the capillaries within or below the dermal layer of the skin for systemic delivery of the drug substance.

As used herein, "deuteration" refers to the substitution of a hydrogen (protium, 1H) atom in a chemical structure with a deuterium atom ($^2$H). A hydrogen atom position of a structure is considered substituted with deuterium when the abundance of deuterium at that position is enriched. The natural abundance of deuterium is about 0.02%, so a compound is "enriched" with deuterium at a specific position when the frequency of incorporation of deuterium at that position exceeds 0.02%. Therefore, in any embodiment of a deuterated compound provided herein, any one or more hydrogen atoms may be enriched with deuterium at a level of greater than 0.1%, or greater than 0.5%, or greater than 1%, or greater than 5%, such as, greater than 50%, or greater than 60%, or greater than 70%, or greater than 80%, or greater than 90% or greater than 95%, or greater than 96%, or greater than 97%, or greater than 98%, or greater than 99%.

In all aspects and embodiments of the present disclosure comprising the Compound of Formula I, said Compound of Formula I may optionally be deuterated at one or more hydrogen atom positions.

In all aspects and embodiments of the present disclosure comprising the Compound of Formula II, said Compound of Formula II is enriched only at the designated positions $(2,2-d_2)$.

In all aspects and embodiments of the present disclosure comprising the Compound of Formula III, said Compound of Formula III is enriched only at the designated positions $(1,1,2,2-d_4)$.

In some embodiments, the formulations may further comprise one or more anti-oxidants, for example, tocopherol, butylated hydroxytoluene (BHT), propyl gallate (OPG), citric acid, and/or ascorbic acid, or the like. In some embodiments, the formulations do not comprise any anti-oxidant compounds. The inclusion of an anti-oxidant may further improve the chemical stability of the formulations by preventing oxidative chemical degradation of the active ingredient.

In another aspect, the present disclosure provides Formulation 1, et seq., Formulation 2, et seq., Formulation 3, et seq., or Device 1, et seq., for use in treating a disease or abnormal condition involving or mediated by the 5-HT$_{2A}$ receptor, serotonin transporter (SERT), and/or dopamine D$_1$/D$_2$ receptor signaling pathways, e.g., a disorder selected from obesity, anorexia, bulimia, depression (including major depressive disorder (MDD)), anxiety, psychosis, schizophrenia, obsessive-compulsive disorder, sexual disorders, migraine, attention deficit disorder, attention deficit hyperactivity disorder, sleep disorders, conditions associated with cephalic pain, social phobias, dementia (including Alzheimer's Disease and Parkinson's dementia), gastrointestinal disorders such as dysfunction of gastrointestinal tract motility and obesity, or bipolar disorder (e.g., bipolar depression).

In another embodiment, the invention provides a method (Method 1) for the prophylaxis or treatment of a disease or abnormal condition involving or mediated by the 5-HT$_{2A}$ receptor, serotonin transporter (SERT), and/or dopamine D$_1$/D$_2$ receptor signaling pathways, in a patient in need thereof, comprising administering to the patient by a transdermal route, a therapeutically effective amount of the Compound of Formula I and/or the Compound of Formula II and/or the Compound of Formula III. Further embodiments of Method 1 include:

1.1 Method 1, wherein the Compound of Formula I and/or the Compound of Formula II and/or the Compound of Formula III is administered via a transdermal route (e.g., administered using a transdermal delivery device, such as a patch, gel, ointment, or spray).

1.2 Method 1.1, wherein the Compound of Formula I and/or the Compound of Formula II and/or the Compound of Formula III is administered in the form of a composition selected from any of Formulation 1, et seq., or Formulation 2, et seq. or Formulation 3, et seq.

1.3 Method 1.1 or 1.2 wherein the Compound of Formula I and/or the Compound of Formula II and/or the Compound of Formula III is administered via Device 1, et seq.

1.4 Method 1 or any of 1.1, et seq., wherein the disease or condition is selected from obesity, anorexia, bulimia, depression (including major depressive disorder (MDD)), anxiety, psychosis, schizophrenia, obsessive-compulsive disorder, sexual disorders, migraine, attention deficit disorder, attention deficit hyperactivity disorder, sleep disorders, conditions associated with cephalic pain, social phobias, dementia (including Alzheimer's Disease and Parkinson's dementia), gastrointestinal disorders such as dysfunction of gastrointestinal tract motility and obesity, or bipolar disorder (e.g., bipolar depression).

1.5 Method 1 or any of 1.1, et seq., wherein the daily dosage administered via the transdermal route (e.g., via Device 1, et seq.) provides from 1 to 50% of the dosage administered for the same condition by the oral route, for example, 1 to 40%, or from 5 to 25%, or from 5 to 15%, or from 1-5%, or from 2.5 to 7.5% of the daily oral dosage (due to reduced first pass and GI metabolism).

1.6 Method 1 or any of 1.1, et seq., wherein the method comprises transdermal application of the transdermal delivery device once every 30 days or less, e.g., once every 20 days or less, or once every 15 days or less, or once every 10 days or less, or once every 7 days or less, or once every 5 days or less, or once every 3 days or less.

1.7 Method 1 or any of 1.1, et seq., wherein the method comprises delivery of the Compound of Formula I or the Compound of Formula II or the Compound of Formula III to the patient at an average daily dosage of from 5 to 60 mg per day (free base equivalent), e.g., 5 to 40 mg per day, or 5 to 30 mg per day, or 5 to 20 mg per day, or 5 to 15 mg per day, or 5 to 10 mg per day, or 1 to 5 mg per day, or 1 to 3 mg per day or 2 to 3 mg per day, or about 1.8 mg per day, or 0.1 to 2 mg per day, or 0.1 to 1 mg per day, or 0.1 to 0.7 mg per day, or about 0.6 mg per day.

A Compound of Formula I or a Compound of Formula II and/or a Compound of Formula III, for use in Method 1 or any of Method 1.1 et seq.

A pharmaceutical composition selected from any of Formulation 1, et seq., Formulation 2, et seq., or Formulation 3, et seq., or Device 1, et seq., for use in Method 1 or any of Method 1.1 et seq.

Use of a Compound of Formula I or a Compound of Formula II or a Compound of Formula III in the manufacture of a medicament for transdermal administration, e.g., a medicament in accordance with any of Formulation 1, et seq., Formulation 2, et seq., or Formulation 3, et seq., or Device 1, et seq., for use in a method of treatment according to Method 1 or any of Method 1.1 et seq.

Methods of synthesizing the Compounds of Formula I and the Compounds of Formula II and III are known in art, and include the methods disclosed in U.S. Pat. Nos. 6,548,493; 7,238,690; 6,552,017; 6,713,471; 7,183,282; 7,081,455; 8,309,722; U.S. RE39680, and U.S. RE39679, and US 2017/183350, the contents of each of which are incorporated by reference in their entirety. Salts of the Compounds of the Invention may also be prepared as similarly described in U.S. Pat. Nos. 6,548,493; 7,238,690; 6,552,017; 6,713,471; 7,183,282; 8,648,077; U.S. RE39680; and U.S. RE39679, the contents of each of which are incorporated by reference in their entirety.

Isolation or purification of the diastereomers of the Compounds of the Invention may be achieved by conventional methods known in the art, e.g., column purification, preparative thin layer chromatography, preparative HPLC, crystallization, trituration, simulated moving beds and the like.

The pharmaceutically acceptable salts of the Compounds of Formula I, II and III can be synthesized from the parent compound which contains a basic or acidic moiety by conventional chemical methods. Generally, such salts can be prepared by reacting the free base forms of these compounds with a stoichiometric amount of the appropriate acid in water or in an organic solvent, or in a mixture of the two; generally, non-aqueous media like ether, ethyl acetate, ethanol, isopropanol, or acetonitrile are preferred. Further details for the preparation of these salts, e.g., toluenesulfonic salt in amorphous or crystal form, may be found in U.S. Pat. No. 8,309,722 and/or U.S. Pat. No. 8,648,077.

Transdermal dosage forms are known to those skilled in the art, and general procedures by which these dosage forms can be prepared have been described. Examples of such delivery systems include those disclosed in U.S. Pat. No. 9,993,466 to Lee et al., U.S. Pat. No. 9,913,840 to Jain et al., U.S. Pat. No. 9,693,970 to Mo, U.S. Pat. No. 9,585,862 to Hwang et al., and U.S. Pat. No. 7,858,114 to Ito. The contents of each of these references is incorporated by reference herein in their entireties.

EXAMPLES

Example 1A: Comparison of Pharmacokinetics Between Subcutaneous (SC) and Sublingual (SL) Dosing in Dogs In vivo absorption and distribution of the Compound of Formula I and the Compound of Formula II, both in their tosylate salt forms, is compared between subcutaneous and sublingual administration in non-cross over sequential studies in dogs.

SC Administration: Six male beagle dogs between 2 and 5 years of age are randomized in two groups of three dogs each. Dogs in group 1 are administered the Compound of Formula I at a dose of 1 mg/kg (free base equivalent) in a 0.5% methylcellulose/distilled water vehicle. Dogs in group 2 are administered the Compound of Formula II at a dose of 1 mg/kg (free base equivalent) in a 0.5% methylcellulose/distilled water vehicle. Administration is subcutaneous in the intrascapular region via a 22 or 23 gauge needle. Whole blood samples are collected via the dog's cephalic vein pre-dose, and at post-dose time-points 5, 15 and 30 minutes, 1, 2, 4, 6, 8 and 24 hours. Following a minimum 7-day washout period, the dogs are transferred to the sublingual portion of the study.

SL Administration: The dogs of group 1 are administered the Compound of Formula I at a dose of 1 mg/kg (free base equivalent) in a 0.5% methylcellulose/distilled water vehicle. Dogs in group 2 are administered the Compound of Formula II at a dose of 1 mg/kg (free base equivalent) in a 0.5% methylcellulose/distilled water vehicle. The animals are anesthetized prior to administration of the dose using propofol (6 mg/kg) and anesthesia is maintained for 30 minutes using 3-4.5% isoflurane. Administration is sublingual and the dosage is applied for 30 minutes, then wiped off using unwoven gauze. Whole blood samples are collected via the dog's cephalic vein pre-dose, and at post-dose time-points 5, 15 and 30 minutes, 1, 2, 4, 6, 8, 24, 36 and 48 hours.

All blood samples are processed to plasma and analyzed for drug concentrations using liquid chromatography-tandem mass spectrometry (LC-MS/MS). Area under the curve (AUC) of parent and metabolites based on plasma versus time data are calculated using Prism 5.04 software (GraphPad Software, Inc.).

The results are summarized in Table 1A below (AUC is shown for 0-24 hours):

|   | Test Compound (1 mg/kg): | Formula I | Formula II |
|---|---|---|---|
| SL | AUC (ng – hr/mL) | 734 | 1262 |
|   | Cmax (ng/mL) | 259 | 562 |
|   | Tmax (hr) | 1.0 | 1.0 |
| SC | AUC (ng – hr/mL) | 813 | 785 |
|   | Cmax (ng/mL) | 110 | 79 |
|   | Tmax (hr) | 1.0 | 1.0 |

The results demonstrate that both SC and SL dosing results in high plasma concentration and high plasma AUC.

SL dosing also results in significantly higher maximal plasma concentration of drug (Cmax) compared to SC dosing for both compounds. For the Compound of Formula II, SL dosing also results in a significantly higher overall AUC, while the AUC for the Compound of Formula I shows comparable AUC between SC and SL dosing. Time to maximum plasma concentration is also the same between SC and SL dosing for both compounds.

Example 1B: Comparison of Pharmacokinetics Between Subcutaneous and Sublingual Dosing in Dogs with Metabolite Analysis A second study is performed substantially as described for Example 1A, except that plasma samples are analyzed for the parent (administered) compounds, as well as for the major known metabolites. After administration of either the Compound of Formula I or the Compound of Formula II, the major circulating species are found to be the parent and the N-desmethyl metabolite. The results are summarized in Table 1B below (AUC is shown for 0-24 hours):

|    | Test Compound (1 mg/kg): | Formula I | Formula II |
|----|--------------------------|-----------|------------|
| SL | AUC (ng – hr/mL)-Parent  | 507       | 1262       |
|    | Cmax (ng/mL)-Parent      | 179       | 562        |
|    | Tmax (hr)-Parent         | 1.0       | 1.0        |
|    | AUC (ng – hr/mL)-Des-methyl | 23     | 104        |
|    | Cmax (ng/mL)-Des-methyl  | 4.0       | 27         |
|    | Tmax (hr)-Des-methyl     | 1.0       | 1.0        |
| SC | AUC (ng – hr/mL)-Parent  | 560       | 785        |
|    | Cmax (ng/mL)-Parent      | 76        | 79         |
|    | Tmax (hr)-Parent         | 1.0       | 1.0        |
|    | AUC (ng – hr/mL)-Des-methyl | 20     | 49         |
|    | Cmax (ng/mL)-Des-methyl  | 4.0       | 1.0        |
|    | Tmax (hr)-Des-methyl     | 1.7       | 1.0        |

These results further demonstrate that both SC and SL dosing results in high plasma concentration and high plasma AUC for the administered compounds. SL dosing also results in higher maximal plasma concentration of drug (Cmax) compared to SC dosing for both compounds. In addition, the results show that both SC and SL dosing results in very low rates of metabolite formation, indicating that these routes effectively bypass the primary site of metabolic degradation of these compounds (hepatic metabolism). The Compound of Formula I circulated in plasma at an AUC approximately 22 times higher for parent than metabolite after SL dosing, and 27 times higher for SC dosing. In contrast, when administered orally, it has been found that the Compound of Formula I and its desmethyl metabolite circulate in plasma with AUC's of about 1:1 or less. Similarly, results are shown for the Compound of Formula II (parent/metabolite ratio of about 12 for SL and about 16 for SC).

Example 2: Pharmacokinetics of Oral Dosing in Dogs

In contrast to the subcutaneous and sublingual pharmacokinetics presented in Example 1, this Example demonstrates that oral administration results in substantially lower systemic exposure to drug, due to the high extent of hepatic first-pass metabolism. This is true even using doses from 2.5 times to 15 times higher than the dose used in the SC and SL study.

As part of a larger long-term toxicology study, 20 male and female beagle dogs are administered either control, or the Compound of Formula I, tosylate salt form, at a dose of 2.5, 5, 10, or 15 mg/kg. For control, the dogs are administered empty capsules. For the Compound of Formula I, the dogs are administered normal-release oral capsules. Blood samples are obtained at 0.25 hours, 0.5 hours, 1 hour, 4 hours, 8 hour and 24 hours. The blood samples are processed to plasma and analyzed for concentration of the Compound of Formula I by high-performance liquid chromatography-mass spectrometry. Cmax, Tmax and area-under-the-curve (AUC, 0-24 hours) are calculated using Phoenix WinNonlin software. The results are shown in Table 1 below:

|                | Dosing: | | | |
|----------------|---------|---------|----------|----------|
|                | 2.5 mg/kg | 5 mg/kg | 10 mg/kg | 15 mg/kg |
| AUC (ng – hr/mL) | 40.05   | 52.45   | 142.5    | 248      |
| Cmax (ng/mL)   | 5.51    | 7.72    | 29.0     | 44.5     |
| Tmax (hr)      | 0.469   | 0.875   | 0.813    | 1.63     |

The Compound of Formula I shows dose-dependent oral absorption, and that the plasma concentration achieved with even the highest-oral dose is far below the plasma concentration and AUC achieved from sublingual and subcutaneous administration as shown in Example 1. Sublingual and subcutaneous dosing of the Compound of Formula I at only 1.0 mg/kg results in 24-hour AUC that is more than 18× higher than oral dosing at 2.5 mg/kg. Sublingual and subcutaneous doing even provide 24-hour AUC about three times higher at 1.0 mg/kg than oral dosing at 15 mg/kg.

These results taken together clearly demonstrate the large loss in exposure resulting from hepatic first pass metabolism, and the unexpectedly high improvement in exposures that are achieved from using transdermal dosing systems.

Example 3: Pharmacokinetics of SC and IV Dosing in Monkeys

A study is also performed in monkeys to determine the plasma concentrations of both the Compound of Formula I and its major metabolites after both SL and SC dosing at 0.5 mg/kg. Six Cynomolgus monkeys are divided into two groups for IV and SC dosing with the Compound of Formula I. The animals are dosed in a fasting state. Blood samples are collected pre-dose, and at 5 minutes, 15 minutes, 1, 2, 4, 6, 8, 24, 36 and 48 hours post-dose. All blood samples are processed to plasma and later analyzed by liquid chromatography-tandem mass spectrometry. Samples are tested for the concentration of the Compound of Formula I, as well as for its five major known metabolites. PK parameters are calculated using PK Solutions 2.0 software (Summit Research Services, Colorado, US).

The results show that bioavailability (based on a comparison of IV to SC pharmacokinetics) is about 74% for the Compound of Formula I or SC administration. Most tested metabolites are found to present at levels below the limit of quantitation. Only the des-methyl metabolite and the amide metabolite (oxidation of the methylene adjacent to the N-methyl group to a carbonyl) are found to be present in significant concentration. The concentrations of both metabolites are found to be lower after SC dosing than after IV dosing. The results are shown in Table 3 below:

|    | Analyte:        | Parent Compound | Des-methyl metabolite | Amide Metabolite |
|----|-----------------|-----------------|-----------------------|------------------|
| IV | AUC (ng – hr/mL) | 297             | 9.2                   | 20               |
|    | Cmax (ng/mL)    | 94              | 1.5                   | 1.9              |
|    | Tmax (hr)       | 0.083           | 1.0                   | 4.0              |

-continued

| Analyte: | | Parent Compound | Des-methyl metabolite | Amide Metabolite |
|---|---|---|---|---|
| SC | AUC (ng – hr/mL) | 220 | 2.3 | 3.3 |
| | Cmax (ng/mL) | 23 | 0.3 | 0.3 |
| | Tmax (hr) | 2.0 | 2.0 | 6.0 |

The results show that SC administration in monkeys results in substantially lower levels of formation of the major metabolites compared to IV administration.

All of the foregoing results demonstrate the effectiveness of administering the compounds of the present disclosure in a manner which avoids first-pass metabolism.

Example 4: In-Vitro Permeation Studies

Dual-layer transdermal patches are prepared which comprise an adhesive drug reservoir layer and a backing layer, protected by a release liner. Permeation studies are performed by removing the release liner from a sample patch, and immediately applying the patch to the stratum corneum layer of human cadaver skin fixed to the donor chamber side of a modified Franz diffusion cell. Mesh is applied over the patch to ensure that it remains adhered to the skin during the length of the experiment. The bottom chamber of the cell contains a receptor solution that is sampled at various time points and analyzed for lumateperone content. The cell includes a magnetic mixer bar to ensure thorough mixing. These measurements are used over the course of the experiment to calculate drug flux and cumulative delivery. All experiments use Franz cells with 2 square centimeter diffusional areas and 5.0 mL receptor solution capacities. The transdermal patches are 1 square centimeter in size. Temperature is maintained at 32° C., and humidity is ambient. The receptor solutions consist of 20% v/v polyethylene glycol 400 in pH 7.4 phosphate buffer. Solution samples are analyzed by HPLC.

Study 1. Patches are prepared comprising a two-component drug reservoir layer, consisting of 2.5% w/w lumateperone free base in a single excipient. 25 excipients are tested Samples from the receptor solutions are taken at 3, 6, 12 and 24 hours after application. Cumulative permeation results are shown in the table below:

| Excipient | Cum. Permation (μg) |
|---|---|
| Lauryl lactate | 90 |
| Isopropyl myristate | 68 |
| Oleayl Oleate | 61 |
| Methyl laurate | 57 |
| Isopropyl palmitate | 48 |
| Ethyl oleate | 44 |
| Octyldodecanol | 38 |
| Propylene glycol | 25 |
| Others | <15 |

The results show that of the 25 excipients selected, eight significantly outperform the other sixteen in promoting. The sixteen other excipients, which all resulted in cumulative permeations of 2-15 μg, are: butylene glycol, diethylene glycol monomethyl ether, diisopropyl adipate, dipropylene glycol, glyceryl monooleate, glycerol, isostearic acid, laureth-4, levulinic acid, octisalate, oleic acid, oleyl alcohol, propylene glycol monolaurate, sorbitan monooleate, and triacetin.

Study 2. Patches are prepared comprising a three-component drug reservoir layer, consisting of 10% w/w lumateperone free base and 20% w/w excipient in a polyacrylate vehicle. The eight preferred excipients from Study 1 are tested, along with a control containing 10% w/w lumateperone free base in polyacrylate vehicle. Samples from the receptor solutions are taken at 6, 24, 48 and 72 hours after application. A significant difference is observed in the presence of excipient compared with the absence of excipient. Optimal results are obtained with lauryl lactate excipient, resulting in 114 μg drug delivery over 72 hours, followed by propylene glycol and methyl laurate (50-70 μg), with the remaining excipients showing results similar to control (all 25-40 μg).

Study 3. Patches are prepared comprising a four-component drug reservoir layer, consisting of 10% w/w lumateperone free base and 0-10% w/w lauryl lactate excipient in a mixed polyacrylate adhesive and silicone adhesive vehicle. Samples from the receptor solutions are taken at 6, 24, 48 and 72 hours after application. As expected, the samples with 0% excipient produce the lowest permeation values, all less than 30 μg at 72 hours, while the samples with 10% excipient produce the highest permeation values, all greater than 70 μg at 72 hours. Optimal results are shown for the combination of 10% lauryl lactate, 40% acrylate adhesive and 40% silicone adhesive.

Further studies. Further studies are performed which examine an additional 20 excipients for their effect on permeation enhancement. Of these additional excipients, only methyl caprate and Labrafac PG® (propylene glycol dicaprate/dicaprylate) are found to significantly enhance permeation.

Further studies also evaluate 10% w/w lumateperone in various excipient mixtures in a polyacrylate/silicone adhesive vehicle. Each mixture includes a combination of excipients selected from lauryl lactate (LL), propylene glycol (PG), methyl laurate (ML), and propylene glycol dicaprate/dicaprylate (PGDD). It is found that there is an unexpected synergistic effect on permeation resulting from the combination of lauryl lactate with propylene glycol, as shown in the summary below:

| Excipient Mixture(s) | Cumulative 72 hr Permation (μg) |
|---|---|
| 10% LL, 1% PG | 170-180 |
| 5% LL, 5% PG, 5% ML, 5% PGDD; | 140-170 |
| 20% LL; | |
| 10% LL, 10% ML; | |
| 10% PG, 10% ML; | 80-110 |
| 10% PG, 10% PGDD; | |
| 20% ML; | |
| 20% PG | |
| 10% ML, 10% PGDD; | 40-60 |
| 20% PGDD | |

Further studies also evaluate dimethyldodecylamine oxide (DDAO) as an enhancing excipient. It is unexpectedly found that add just 2 wt % DDAO to the formulation comprising 20% lumateperone, 15% lauryl lactate, and 10% propylene glycol results in nearly a doubling of permeation at 72 hours, from about 300 μg to more than 550 μg.

It was further unexpectedly found that lactic acid enhances permeation. This is believed to result from its interfere with cohesion of the adhesive matrix. Comparative studies are further performed and show that lactic acid produces more favorable enhancement of permeation than the similar acids glycolic acid, mandelic acid and tropic acid.

Finally, six final drug reservoir layer formulations each having 20 wt % lumateperone are tested in a swine 3-day irritation and drug delivery study. Patches are also tested for stability in a 2-month aging study. For the swine studies, approximately 2"×2" patches are placed adjacent in series on the animal's back, with the edges taped down with medical adhesive tape. An additional adhesive-only control is used for comparison of irritation results. Drug delivery is determined by measuring the amount of drug remaining in the patch and on the surface of the skin (collected by swabbing) compared to the amount of drug originally present in each patch (which varied slightly with the exact size of each patch). The six formulations are shown in the table below (w/w %).

|  | 1 | 2 | 3 | 4 | 5 | 6 |
|---|---|---|---|---|---|---|
| Lumateperone | 20% | 20% | 20% | 20% | 20% | 20% |
| Lauryl Lactate | 14% | 14% | 14% | 14% | 15% | — |
| Propylene Glycol | 10% | 10% | 10% | 10% | 10% | — |
| DDAO | — | 1% | 2% | 3% | 2% | — |
| Lactic Acid | 1% | 1% | 1% | 1% | — | — |
| Ascorbyl Palmitate | 1% | 1% | 1% | 1% | 1% | — |
| Adhesive | Q.S. | Q.S. | Q.S. | Q.S. | Q.S. | Q.S. |
| Drug Delivery | 51% | 57% | 61% | 62% | 49% | 13% |

All six formulations show similar irritation and stability results: there is no significant irritation or discoloration of the skin after 72 hours of application (comparable to control) and the patches show <0.3% degradation on storage at room temperature for up to 2 weeks. On storage at room temperature for up to 2 months, the patches show degradation of 0.1 to 0.7%. Lumateperone is thus stable on room temperature storage in these patch formulations, and the patch formulations are not significantly irritating to the skin. Drug delivery results show that both lactic acid and DDAO enhance in vivo delivery with an unexpected synergistic effect compared to excipient-only patches. Patches lacking any excipient (adhesive only) show very poor drug delivery.

What is claimed:

1. A transdermal pharmaceutical formulation comprising 1-(4-fluoro-phenyl)-4-((6bR,10aS)-3-methyl-2,3,6b,9,10,10a-hexahydro-1H,7H-pyrido [3',4': 4,5]pyrrolo[1,2,3-de]quinoxalin-8-yl)-butan-1-one (Compound of Formula I) in free base, co-crystal or salt form, or comprising 1-(4-fluoro-phenyl)-4-((6bR,10aS)-2,2-$d_2$-3-methyl-2,3,6b,9,10,10a-hexahydro-1H,7H-pyrido[3',4': 4,5]pyrrolo[1,2,3-de]quinoxalin-8-yl)-butan-1-one (Compound of Formula II) in free base, co-crystal or salt form, or comprising 1-(4-fluoro-phenyl)-4-((6bR,10aS)-1,1,2,2-$d_4$-3-methyl-2,3,6b,9,10,10a-hexahydro-1H,7H-pyrido[3',4': 4,5]pyrrolo[1,2,3-de]quinoxalin-8-yl)-butan-1-one (Compound of Formula III) in free base, co-crystal or salt form;
wherein the formulation is comprised in a patch;
and wherein the formulation further comprises one or more excipients selected from lauryl lactate, isopropyl myristate, oleayl oleate, methyl laurate, isopropyl palmitate, and ethyl oleate.

2. The formulation of claim 1, wherein the formulation comprises the Compound of Formula I or the Compound of Formula II or the Compound of Formula III in free base form.

3. The formulation of claim 1, wherein the formulation comprises the Compound of Formula I or the Compound of Formula II or the Compound of Formula III in pharmaceutically acceptable salt form.

4. The formulation of claim 3, wherein the salt form is tosylate salt form.

5. The formulation of claim 1, wherein the formulation comprises from 1 to 1000 mg of the Compound of Formula I or the Compound of Formula II or the Compound of Formula III, wherein the amount is measured as the free base equivalent.

6. The formulation of claim 1, further comprising one or more excipients selected from the group consisting of solvents, solubilizers, plasticizers, surfactants, binders, humectants, antioxidants, buffering agents, emollients, and thickening agents.

7. The formulation of claim 6, wherein the one or more excipients are selected from any of the following: alcohols, non-alcoholic solvents, gums, polysaccharides and polysaccharide derivatives, gelatins, polyvinylpyrrolidones, polyethylene oxide and/or polypropylene oxide polymers and copolymers, polyacrylate polymers, polyamide polymers, sugars and sugar alcohols, polypeptides/proteins, amino acids, inorganic or organic acids and their salts and esters, inorganic or organic bases, anionic surfactants, cationic surfactants, zwitterionic surfactants, nonionic surfactants, sorbitan esters, polyethoxylated sorbitan esters, fatty acid esters, fatty alcohols, and antioxidants.

8. The formulation of claim 1, wherein the patch is an adhesive patch and the formulation comprises an adhesive polymer.

9. The formulation of claim 8, wherein the adhesive polymer comprises a polymer selected from the group consisting of acrylate polymers or co-polymers; polyvinylpyrrolidones, copolymers of maleic acid or a maleic ester with a vinyl ether, cellulose derivatives, silicone polymers, and mixtures thereof.

10. The formulation of claim 1, wherein the formulation comprises the Compound of Formula I in free base form.

11. The formulation of claim 1, wherein the patch is an adhesive patch.

12. A transdermal pharmaceutical device comprising the formulation according to claim 1, wherein the device comprises at least two layers, wherein at least one layer is a drug reservoir layer, and at least one layer is a backing layer.

13. The device of claim 12, wherein the drug reservoir layer comprises the one or more excipients selected from lauryl lactate, isopropyl myristate, oleayl oleate, methyl laurate, isopropyl palmitate, and ethyl oleate.

14. The device of claim 12, wherein the drug reservoir layer comprises an adhesive polymer, and wherein the drug reservoir layer is the skin-contacting layer of the device.

15. The device of claim 12, wherein the device further comprises a third layer, separate from the drug reservoir layer, which third layer is the skin-contacting layer and which layer comprises an adhesive polymer, and which layer is substantially free of the Compounds of Formula I, Formula II and Formula III prior to use of the device.

16. The device of claim 15, wherein the device further comprises an intermediate layer disposed between the skin contacting layer and the drug reservoir layer, which layer is a rate-control layer.

17. The device of claim 15, wherein the drug reservoir layer and/or the skin-contacting layer comprises the one or more excipients selected from lauryl lactate, isopropyl myristate, oleayl oleate, methyl laurate, isopropyl palmitate, and ethyl oleate.

18. The device of claim 12, wherein the device comprises from 1 to 1000 mg of the Compound of Formula I or the Compound of Formula II or the Compound of Formula III, wherein the amount is measured as the free base equivalent.

19. The device of claim 12, wherein the device is formulated to deliver the Compound of Formula I or the Compound of Formula II or the Compound of Formula III to a patient over a period of time from 1 to 30 days.

20. The device of claim 12, wherein the device is formulated to deliver the Compound of Formula I or the Compound of Formula II or the Compound of Formula III to a patient at an average daily dosage of from 1 to 60 mg per day, wherein the amount is measured as the free base equivalent.

21. The device of claim 12, wherein the device systemically delivers a mean daily dose of the Compound of Formula I or the Compound of Formula II or the Compound of Formula III of 0.1 to 5.0 mg per day, wherein the amount is measured as the free base equivalent.

22. The device of claim 12, wherein the device delivers the Compound of Formula I or the Compound of Formula II or the Compound of Formula III at a rate sufficient to maintain a steady state maximum plasma concentration of the compound of 5 to 50 ng/ml and/or sufficient to maintain a steady state 24-hour mean plasma concentration area under the curve (AUC) of the compound of 5 to 100 ng-hr/mL, wherein the concentration is measured as the free base equivalent.

23. A method for the prophylaxis or treatment of a disease or abnormal condition involving or mediated by the 5-HT$_{2A}$ receptor, serotonin transporter (SERT), and/or dopamine D$_1$/D$_2$ receptor signaling pathways, in a patient in need thereof, comprising administering to the patient by a transdermal route, a therapeutically effective amount of the formulation according to claim 1.

24. The method according to claim 23, wherein the disease or condition is selected from obesity, anorexia, bulimia, depression, anxiety, psychosis, schizophrenia, obsessive-compulsive disorder, sexual disorders, migraine, attention deficit disorder, attention deficit hyperactivity disorder, sleep disorders, conditions associated with cephalic pain, social phobias, dementia, bipolar disorder, and bipolar depression.

25. The formulation of claim 1, wherein the one or more excipients are selected from lauryl lactate and methyl laurate,.

26. The formulation of claim 7, wherein the one or more excipients are selected from any of the following: ethanol, isopropanol, propanol, glycerol, propylene glycol, butylene glycol, pentylene glycol, hexylene glycol, polyethylene glycol, dimethylsulfoxide, dimethylformamide, acetonitrile, acacia gum, guar gum, agar, xanthan gum, tragacanth gum, karaya gum, gellan gum, starches, dextrans, pectins, alginates, carrageenans, cellulose, cellulose derivatives, bovine gelatins, porcine gelatins, avian gelatins, fish gelatins, poloxamers, carbopols, dextrose, lactose, galactose, glucose, ribose, sucrose, trehalose, mannitol, maltitol, lactitol, sorbitol, xylitol, erythritol, galactitol, inositol; benzoic acid, toluenesulfonic acid, phosphoric acid, sulfuric acid, hydrochloric acid, tartaric acid, oxalic acid, cyclamic acid, ascorbic acid, methanesulfonic acid, benzenesulfonic acid, formic acid or their sodium, potassium, calcium, magnesium, lithium, ammonium salts; sodium lauryl sulfate, sodium laureth sulfate, sodium dodecylbenzenesulfonate, sodium lauroyl sarcosinate, sodium stearate, benzalkonium halides, cetylpyridinium halides, cetrimonium halides, benzethonium halides, cocamidopropyl betaine, polyethylene glycol polydodecyl ethers, sorbitan monolaurate, sorbitan monooleate, sorbitan monopalmitate, sorbitan monostearate, sorbitan tristearate, polysorbate 20, polysorbate 40, polysorbate 60, polysorbate 80, dodecanol, octyldecanol, lauryl alcohol, ascorbic acid, citric acid, ascorbyl palmitate, sodium metabisulfite, BHT, BHA, TBHQ, propyl gallate, beta-carotene, tocopherols, and tocotrienols.

27. The formulation of claim 26, wherein the cellulose derivatives are selected from carboxymethyl cellulose, methylcellulose, hydroxyethyl cellulose, hydroxypropyl cellulose, and hydroxypropyl methyl cellulose.

28. The formulation of claim 9, wherein the adhesive polymer comprises a polymer selected from the group consisting of acrylate polymers or co-polymers, linear polyvinylpyrrolidones, cross-linked polyvinylpyrrolidones, copolymers of maleic acid or anhydride with methyl vinyl ether, carboxymethyl cellulose, dimethylsilicone, and mixtures thereof.

29. The formulation of claim 9, wherein the adhesive polymer comprises a mixture of a polyacrylate polymer and a silicone polymer.

30. The formulation of claim 1, wherein the formulation further comprises either dimethyldodecyl amine oxide or lactic acid.

31. The formulation of claim 30, wherein the formulation further comprises propylene glycol.

* * * * *

UNITED STATES PATENT AND TRADEMARK OFFICE
CERTIFICATE OF CORRECTION

| | | |
|---|---|---|
| PATENT NO. | : 12,144,808 B2 | Page 1 of 1 |
| APPLICATION NO. | : 17/271965 | |
| DATED | : November 19, 2024 | |
| INVENTOR(S) | : Li et al. | |

It is certified that error appears in the above-identified patent and that said Letters Patent is hereby corrected as shown below:

In the Specification

Column 1, Lines 11-12, "is are incorporated herein by reference in its entirety their entireties" should be changed to "are incorporated by reference in their entireties."

Signed and Sealed this
Second Day of December, 2025

John A. Squires
*Director of the United States Patent and Trademark Office*